United States Patent [19]

Tang et al.

[11] Patent Number: 4,920,203

[45] Date of Patent: Apr. 24, 1990

[54] MEDICAL DEVICES FABRICATED FROM HOMOPOLYMERS AND COPOLYMERS HAVING RECURRING CARBONATE UNITS

[75] Inventors: Reginald T. Tang, Warren; Frank Mares, Whippany; William J. Boyle, Jr., Parsippany; Tin-Ho Chiu, Millburn; Kundabhai M. Patel, Landing, all of N.J.

[73] Assignee: Allied-Signal Inc., Morris Township, Morris County, N.J.

[21] Appl. No.: 227,386

[22] Filed: Aug. 2, 1988

Related U.S. Application Data

[63] Continuation-in-part of Ser. No. 134,290, Dec. 17, 1987, and a continuation-in-part of Ser. No. 134,321, Dec. 17, 1987, Pat. No. 4,891,263, and a continuation-in-part of Ser. No. 134,339, Dec. 17, 1987.

[51] Int. Cl.$^5$ ............................................. C08L 71/02
[52] U.S. Cl. .................................. 525/409; 523/105; 523/111; 523/115; 523/113; 525/186; 525/187; 525/403; 525/411; 525/413; 525/415; 528/354; 528/370
[58] Field of Search ............... 528/354, 370; 523/111, 523/105, 113, 115; 128/334, 335.5; 525/461, 411, 413, 415, 409

[56] References Cited

U.S. PATENT DOCUMENTS

| | | | |
|---|---|---|---|
| 3,301,824 | 1/1967 | Hostettler et al. | 528/370 X |
| 3,301,825 | 1/1967 | Hostettler et al. | 260/77.5 |
| 3,305,605 | 6/1967 | Hostettler et al. | 525/186 |
| 3,324,070 | 6/1967 | Hostettler et al. | 525/468 X |
| 3,379,693 | 4/1968 | Hostettler et al. | 525/418 |
| 4,243,775 | 1/1981 | Rosensaft et al. | 524/415 |
| 4,705,820 | 11/1987 | Wang et al. | 524/381 |
| 4,791,929 | 12/1988 | Jarrett et al. | 128/335.5 |

FOREIGN PATENT DOCUMENTS 1604177  12/1981  United Kingdom .
1604178  12/1981  United Kingdom .

OTHER PUBLICATIONS

Makromol. Chem. 187, (1986), pp. 2579–2589.

*Primary Examiner*—Theodore E. Pertilla
*Attorney, Agent, or Firm*—Richard C. Stewart; Gerhard H. Fuchs

[57] ABSTRACT

This invention relates to medical devices formed totally or in part from homopolymers or copolymers comprising recurring carbonate moieties.

38 Claims, No Drawings

| Lane | Preclearing Adsorbant | Final Adsorbant | Band Density | % Depletion |
|---|---|---|---|---|
| 1 | mIgG1 | mIgG2a | 310 | -- |
| 2 | mIgG1 | 32 | 217 | -- |
| 3 | mIgG2a | 32 | 23 | 89 |
| 4 | 32 | mIgG2a | 85 | 73 |
| 5 | 32 | 32 | 42 | 81 |
| 6 | mIgG2a | mIgG2a | 23 | 93 |

FLUORESCENCE INTENSITY UNITS
(Logarithmic Scale)

MEDICAL DEVICES FABRICATED FROM HOMOPOLYMERS AND COPOLYMERS HAVING RECURRING CARBONATE UNITS

RELATED APPLICATIONS

This application is a continuation-in-part application of U.S. patent application Ser. Nos. 134,290, 134,321, now U.S. Pat. No. 4,891,263 and 134,339, each filed Dec. 17, 1987.

FIELD OF THE INVENTION

This invention relates to totally and partially bioresorbable devices capable of degrading into biologically innocuous components and to biodurable medical devices suitable for contacting blood and/or living systems. More particularly, this invention relates to such devices which are fabricated totally or in part from copolymers and homopolymers having recurring carbonate moieties.

BACKGROUND OF INVENTION

Polycarbonates have been known for a number of years. U.S. Pat. No. 3,301,824 describes the preparation of carbonate homopolymers and random copolymers with cyclic lactones. While the patent generally discloses the polymers as having utility in the molding, coating, fiber and plasticizing fields, there is no appreciation whatsoever of biodegradable and/or bioresorbable devices composed in whole or in part of polycarbonate.

Non-bioresorbable synthetic permanent vascular grafts have been available and are made of either Dacron (polyethylene terephthalate) or microporous Teflon (polytetrafluoroethylene). Various prostheses such as grafts, and especially those of small diameters for use in coronary bypass procedures, must have certain properties. These properties include physical and mechanical compatibility with the vessel to which they are connected, suturability, compliancy, ability to withstand pressure and pressure fluctuations, and flexibility. Required properties also include biocompatibility, sterilizability, and low toxicity, allergenicity, and mutagenicity. Still other required properties include durability, both in terms of "shelf life" after fabrication and appropriate durability after implantation. Problems which arise from a mismatch of a native vessel and a prosthesis include dilation which may result in aneurysm formation and anastomotic hyperplasia, kinking and the like. Vascular grafts having internal diameters of 8 mm or more and made of biodurable materials have so far been the only successful prostheses for providing a conduit for maintaining continuous blood flow while inflicting a minimal hematologic trauma. Vascular grafts made of Dacron in current clinical use are constructed of knitted or woven Dacron fibers with open pores in the fabric which have to be closed or diminished by preclotting before implantation. Such prostheses have been used as vascular replacements, but only for the relatively larger arteries.

Bioresorbable polymers have been used in the fabrication of devices for implantation in living tissue for several decades. Medical application of such polymers include absorbable sutures, haemostatic aids and, recently, intraosseous implants and control-release drug delivery systems, to name but a few. Use of such polymers has been extended to tissue regeneration devices such as nerve channels, vascular grafts, sperm duct channels, fallopian tube ducts or channels and the like. To be effective, these devices must be made from materials that meet a wide range of biological, physical and chemical prerequisites. The material must be bioresorbable at least in part, nontoxic, noncarcinogenic, nonantigenic, and must demonstrate favorable mechanical properties such as flexibility, suturability in some cases, and amenability to custom fabrication.

Various polymers have been proposed for use in the fabrication of bioresorbable medical devices. Examples of absorbable materials used in nerve repair include collagen as disclosed by D. G. Kline and G. J. Hayes, "The Use of a Resorbable Wrapper for Peripheral Nerve Repair, Experimental Studies in Chimpanzees", *J. Neurosurgery*" 21, 737 (1964). Artandi et al., U.S. Pat. No. 3,272,204 (1966) reports the use of collagen protheses that are reinforced with nonabsorbable fabrics. These articles are intended to be placed permanently in a human body. However, one of the disadvantages inherent with collagenous materials, whether utilized alone or in conjunction with biodurable materials, is their potential antigenicity.

U.S. Pat. Nos. 4,033,938 and 3,960,152 disclose bioabsorbable polymers of unsymmetrically substituted 1,4-dioxane-2,5-diones which the patent broadly states are useful as tubes or sheets for surgical repair such as nerve and tendon splicing. A similar disclosure is in U.S. Pat. No. 4,074,366 relates to poly(N-acetyl-D-glucosamine), i.e., chitin.

Other biodegradable polymers of particular interest for medical implantation purposes are homopolymers and copolymers of glycolic acid and lactic acid. A nerve cuff in the form of a smooth, rigid tube has been fabricated from a copolymer of lactic and glycolic acids [*The Hand*; 10 (3) 259 (1978)]. European patent application 118-458-A discloses biodegradable materials used in organ protheses or artificial skin based on poly-L-lactic acid and/or poly-DL-lactic acid and polyester or polyether urethanes.

U.S. Pat. No. 4,481,353 discloses bioresorbable polyester polymers, and composites containing these polymers, that are also made up of alpha-hydroxy carboxylic acids, in conjunction with Krebs cycle dicarboxylic acids and aliphatic diols. These polyesters are useful in fabricating nerve guidance channels as well as other surgical articles such as sutures and ligatures.

U.S. Pat. Nos. 4,243,775 (1981) and 4,429,080 (1984) disclose the use of polycarbonate-containing polymers in certain medical applications, especially sutures, ligatures and haemostatic devices. However, this disclosure is clearly limited only to "AB" and "ABA" type block copolymers where only the "B" block contains poly(trimethylene carbonate) or a random copolymer of glycolide with trimethylene carbonate and the "A" block is necessarily limited to glycolide. In the copolymers of this patent, the dominant portion of the polymer is the glycolide component.

SUMMARY OF THE INVENTION

The present invention relates to a bioresorbable or biodurable medical device fabricated totally or in part from a biopolymer selected from the group consisting of homopolymers or copolymers having at least one type of recurring monomeric unit of the Structures I and II:

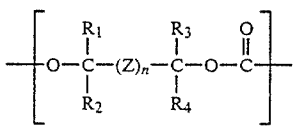

Structure I

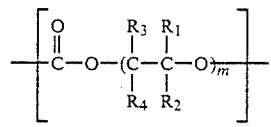

Structure II wherein:

Z is —C(R$_5$R$_6$)—, —NR$_5$—, —O— or a combination thereof, where Z is selected such that there are no adjacent heteroatoms;

n is from 1 to about 8;

m is from 1 to about 8;

R$_1$, R$_2$, R$_3$, and R$_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, alkyl, aryl, alkylcarbonylalkyl, arylcarbonylaryl, alkylcarbonylaryl, alkoxyalkyl, or aryl or alkyl substituted with one or more biologically compatible substituents such as alkyl, aryl, alkoxy, aryloxy, dialkylamino, diarylamino, alkylarylamino substituents;

R$_5$ and R$_6$ are the same or different at each occurrence and are R$_1$, R$_2$, R$_3$, R$_4$, dialkylamino, diarylamino, alkylarylamino, alkoxy, aryloxy, alkanoyl, or arylcarbonyl; or any two of R$_1$ to R$_6$ together can form an alkylene chain completing a 3, 4, 5, 6, 7, 8 or 9 membered alicyclic, fused, spiro, bicyclic and/or tricyclic ring system, which system may optionally include one or more non-adjacent carbonyl, oxa, alkylaza, or arylaza groups; with the proviso that when said biopolymer is a copolymer having recurring monomeric units of the Structure I derived from trimethylene carbonate, the other recurring monomeric units of said copolymer are not derived from glycolide or glycolic acid and with the proviso that when said biopolymer is a homopolymer having recurring monomeric units of the Structure II derived from ethylene carbonate and propylene carbonate, m is other than 1.

The biopolymers used in the practice of this invention exhibit various physical and morphological properties which enable their use in the fabrication of a large number of medical devices. For example, the biopolymers used in the practice of this invention may be crystalline to semi-crystalline to amorphous, having varying modulus and tensile strength. Certain biopolymers of this invention which exhibit high modulus, high tensile strength and relatively slow rates of bioresorbabilities which can be conveniently processed to form high strength medical devices and fibers of various deniers where high strength and slow rates of bioresorbabilities are critical to the efficacy of the device. The device may be implanted in humans to aid in tissue regeneration, growth and/or healing, or may be used outside of the body but in contact with living tissue, body fluids and/or blood without undue adverse impact on such tissue, fluids and/or blood. Other biopolymers used in the practice of this invention are amorphous, soft and pliable materials having relatively fast rates of bioresorbability which can be fabricated into solid medical devices, thin films, coatings and the like where softness and pliability are necessary requirements for the efficacy of the device. Yet other biopolymers used in this invention are strong, elastic and pliable materials having intermediate or slower rates of bioresorbability which can be fabricated into devices such as nerve channels, vascular graft body, sutures, tendon or ligament replacements and the like, where elasticity, strength, pliability and an intermediate or slow rate of bioresorbability are necessary requirements for efficacy of the device. Still others biopolymers used in this invention are elastomeric which allow their use in the fabrication of elastic fibers and medical devices, coatings, films and the like where certain elasticity is critical for efficacy.

The biopolymers for use in the fabrication of the device of this invention exhibit controllable bioresorbability and biodegradation rates, blood compatability, and biocompatibility with living tissue. These biopolymers also induce minimal inflammatory tissue reaction. The biodegradation of the biopolymers used to fabricate the biodegradable devices of this invention usually results in degradation products having a physiologically neutral or relatively neutral pH. Various properties of the biopolymers used in the practice of this invention render devices made from the biopolymers especially suitable for medical applications including but not limited to fabrication of the bioresorbable and biodurable medical devices, such as vascular grafts, stents, fallopian tubes, sperm ducts, wound and skin covers, sutures, hemostatic aids, materials for tendon or ligament repair, bone or dental repair, tubing and parts which are intended to contact the blood, fluids and/or tissue of a living system, e.g., tubings and parts for use in an extracorporeal loop, and biodurable tubings and parts implantable into a living system.

As used herein, "living system" is a living cell, animal or plant, whatever phylogenetic level in the plant or animal kingdom.

As used herein, "biologically innocuous components" are components which may be contacted or implanted into living systems without inducing an adverse reaction and/or components which may be metabolized by the living systems.

As used herein, the term "biodegradable" means capable of being broken down into products by a living system.

As used herein, "homopolymer" is a polymer having the same repeating monomeric unit throughout its structure, which unit is of the Structure I or II as described above.

As used herein, "copolymer" is a polymer having at least two dissimilar repeating monomeric units throughout its structure which are distributed randomly or in a block fashion at least one of which is of the Structure I or II.

As used herein, "medical device" is a device used within or without a human body or animal body to achieve certain medical benefits or goals.

As used herein, "bioresorbable" is capable of being broken down and metabolized by a living system.

As used herein, the term "biopolymer" is a homopolymer and/or copolymer collectively.

As used herein, "biocompatible" is the capability to exist or coexist inside or in close contact with the living systems without adversely impacting the system.

As used herein, "biodurable" means that the device is substantially not biodegradable or bioresorbable.

DETAILED DESCRIPTION OF THE INVENTION

Figure 1:
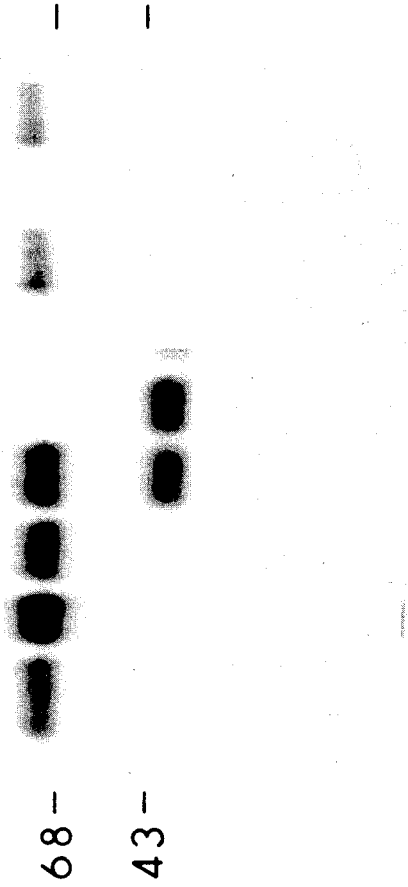

This invention is directed to medical devices. The medical devices of this invention may be biodurable, or may be totally or partially bioresorbable and/or biodegradable. The devices of the invention are fabricated totally or in part of at least one biopolymer of this invention or a combination thereof. The biopolymers may be used to fabricate the total device, or may be use to fabricate only a part of the device, for example, as a coating or a layer or in a mixture with other materials. The only requirement is that the device is fabricated wholly or partially from at least one biopolymer comprising at least one type of recurring monomeric unit of the General Structure I or II.

The devices of this invention can be fabricated into solid articles using conventional techniques for fabricating parts from thermoplastic polymers such as injection molding, melt extrusion, solution extrusion, gel extrusion and the like. Fibrous devices of this invention can be fabricated from the fibers of this invention using conventional techniques for forming woven, knitted or like articles from fibers made of synthetic polymers, and the fibers in turn can be formed using conventional fiber-forming techniques such as melt spinning, gel spinning, solution spinning, dry spinning and the like. These conventional procedures are well known in the art and will not be described herein in any great detail.

The devices of this invention may take many forms and have varying degrees of bioresorbability and/or biodegradability, depending on intended use. For example, the devices of this invention may be solid articles, or may be fibrous devices constructed of woven or non-woven fabric made of fibers formed from the biopolymers of this invention or may be combination of solid and fibrous portions. For example, the device of this invention may be fabricated from fibers and/or yarns which have been woven, braided and/or knitted into fabrics having various structural configurations using conventional means, which fabrics may then be used to fabricate a device, such as a wound cover, gauze, and a vascular graft. The device may be a solid part which has been fabricated into the desired shape using a conventional technique for fabricating parts out of thermoplastics, such as extrusion, molding and solution casting, such as an extruded hollow tubular nerve channel or extruded hollow vascular graft, or a stent for use in angioplasty. The device may also be a composite device having a body which is composed of a woven fabric or a solid part which may or may not be formed from one or more biopolymers of this invention coated with one or more biopolymers of this invention using such techniques as moldings, solution dipping and solution coating; or the device may be a layered device in which one or more layers are formed from the biopolymers of this invention. Illustrative of useful devices of this invention are orthopedic and fracture fixation devices such as maxillo facial repair implants, intraosseous implants, pins, clamps, screws and plates; vascular implants such as vascular grafts; wound closing device such as sutures, fasteners, clips and staples; nerve channels; vascular stents; and the like. Illustrative of still other devices within the scope of this invention are devices for tendon and ligament replacement, breast prostheses, wound and burn covering, dental repair, sponges, tracheolar replacements, hernia patches, absorbant swabs, fallopian tube and sperm ducts, drug delivery devices and the like.

The rate of bioresorption and/or biodegradation exhibited by the device of this invention will vary depending on the desired longevity of the device. For example, because of the relatively high degree of compatibility between the biopolymers used in the construction of the device of this invention and blood and tissue of living systems, one device of this invention is a conventional part which contacts blood or living tissue such as tubing of an extracorporeal loop or other types of flow-through systems for blood, heart valves and the like. In such instances, the device should be formed or at least have a surface which will contact the blood and/or the living tissue coated with a biopolymer having a relatively slow rate of bioresorbability and/or biodegradeability or which is even relatively biodurable. On the other hand, another device of this invention is a vascular graft composed of a fabric composed of a relatively biodurable material such as Dacron or a bioresorbable biopolymer having a relatively slow rate of bioresorption coated with a relatively fast bioresorbing biopolymer, especially in the inside of the graft. The use of the coating having fast rate of bioresorption provides for a regenerated blood vessel having a high degree of patency and relatively low rate of thrombosis.

In one preferred embodiment of this invention, the devices are composed of solid articles which are fabricated from the biopolymers through use of conventional techniques such as injection molding, gel or melt extrusion and the like for fabricating solid articles from thermoplastic polymers. These techniques are well known in the art and will not be described herein in any great detail. For example, such techniques are described in Encyclopedia of Polymer Science and Technology, InterScience, N.Y. The preferred solid devices of this invention are relatively biodurable tubing and coatings which will contact the blood or tissue of a living system, biresorbable and/or biodegradable orthopedic pins and plates, extruded wound and burn coverings, extruded nerve growth channels, extruded fibers for use in tendon and ligament repair.

In another preferred embodiment of the invention, the devices are fibrous devices fabricated totally from fibers composed of the biopolymers of this invention. The fibers, which are also devices of this invention, are prepared by any suitable fiber-forming technique, and the fibers can then be fabricated into useful medical devices using conventional techniques. For example, fibers made from the biopolymers may be formed by conventional processes such as spinning techniques, including melt, solution, dry and gel.spinning. Illustrative of suitable fiber spinning processes and melt spinning techniques and apparatus for carrying out these processes are those described in "Man Made Fibers Science and Technology", Vol. 1-3, H. F. Mark et al., Interscience, N.Y., 1968; "Encyclopedia of Polymer Science and Technology", Vol. 3; Fundamentals of Fiber Formation by Androzej Ziabuke, Wiley and Sons, New York, N.Y. (1976); and "Encyclopedia of Polymer Science and Technology", Vol. 3, pps. 326-381.

The physical characteristics of the fiber may vary widely depending on intended use. For example, the fiber may have any cross-sectional shapes, and may be circular, oval, rectangular, Y-shaped, dog-bone, hexalobal, trilobal, oblong, semi-torroidal, semispherical, semi-arched or the like. Fibers having a circular or oval cross-section may be useful in wound closing applications; and fibers having a multilobal cross-section may be useful as filter components for blood in an extracorporeal loop or otherwise. Similarly, other cross-sectional dimensions of the fiber such as number of lobes, porosity, whether the fiber is solid or hollow and surface properties such as roughness, smoothness, striations on the long axis, as well as circumferential ridges and valleys may also vary depending on the intended use. For example, smooth fibers having a solid cross-section may be important for fabrication of devices such as vascular graft; striated fibers may be used in the fabrication of devices as ligament or tendon prosthesis to encourage certain alignment of cells; and hollow fibers and multilobal fibers may be useful in the fabrication of devices where absorbancy is needed.

Fiber size is not critical and may also vary widely depending on the intended use. For example, fiber size may vary from sub-denier to ribbons and tapes. The effective diameter of the fiber will usually vary from about 0.003 mm to about 6.0 mm. An effective diameter from about 0.003 mm to about 4.0 mm is preferred.

The fibers of this invention may also have a multicomponent construction in which at least one component is composed of one or more of the biopolymers. These fibers include, but are not limited to, sheath-core and multiple component fibers, multilayered types of fiber, hollow fibers and tubes having multicomponent layered construction and the like. These multicomponent fibers are usually formed by co-extrusion of two or more biopolymers or one biopolymers and other materials. Such co-extrusion techniques are known in the art and will not be described in any detail.

The fibers of this invention may also be porous. These fibers can be formed by the addition of fillers, binders, additives and components which were added to the biopolymer before or during fiber formation which are removed or leached from such fibers at some stage to form a porous or semi-porous system. In addition, gas foaming during the extrusion of the fibers either by gaseous foaming agents e.g., $N_2$, He, Ar, Ne, Air, and the like, or chemical foaming agents can be utilized to achieve a porous or somewhat porous structure.

The fibers of this invention may be used in monofialment form as for example as a suture or a nerve channel which is extruded as a hollow fiber. Alternatively, the monofilament fiber of this invention may be towed, braided or twisted from one or more types of fibers, which are then woven, braided and/or knitted into a variety of fibrous medical devices of this invention such as braided, knitted, woven or felted, fabrics or fibrillar products. These fibrous devices can be used as is or coated with other polymers or biopolymers prior to use.

Other characteristics of the fiber, such as denier, modulus, softness, tensile strength and the like depend on the end use of the fiber. For example, softened fibers are preferred in certain applications such as wound dressing, swabs, wound or burn covers, vascular grafts, and the like. Fiber of different or the same polymeric compositions and physical and mechanical properties but differing in denier can be obtained and used or fabricated into fabric that is woven, knitted, velvet, velour, mesh or braided. Staple fibers can be obtained and processed to fabric such as felt, mat and the like. For example, the felted material may be used as, or be part of, skin or wound covers, reinforcements for suturing in surgery, and as aids for hemostasis. Velveted material is particularly suited for use in small caliber blood vessel replacements. Matted fabric may be used, for example, as swabs.

The fibers of this invention are preferably used in the fabrication of implantable bioresorbable medical devices such as vascular implants, nerve channels; burn and wound covers; facial substitutes; orthopedic substitutes for bone or bone repair; breast prostheses; tendon and ligament replacements; hernia patches; and the like, or used as sutures and fasteners. Other devices not necessary for implantation purposes can also be formed from the fibers of this invention. The devices include cell culture substrates, absorbants or swabs, medicated dressings, gauze, fabric, sheet, felt or sponge for hemostasis, dental packs and the like. Particularly useful devices are woven or knitted fabrics formed into tubes of varying shapes, lengths and diameters. Illustrative of these devices are tubular prostheses such as vascular grafts, nerve guidance channels and the like. The particular configuration of such tubes may vary according to the size and shape of the organ to be repaired, and whether the intended repair is to take place in human surgery or in surgery involving other animal species.

Particularly preferred devices of this invention are solid extruded and fibrous vascular repair grafts. Such grafts can be fabricated in conventional configurations as for example as hollow tubes and tubular devices formed from fabrics and the like, using conventional techniques as for example extrusion, weaving, knitting and the like. For vascular graft applications, the internal diameter commonly found useful is in the range of from about 1.0 mm to about 30 mm.

In the preferred embodiments of the invention, especially for vascular graft applications, the device is pretreated to provide a more complaint prostheses. Any conventional method can be used. One preferred pretreatment method is crimping. Illustrative of useful crimping methods is the method described in U.S. Pat. No. 3,337,673. In this method, the spacing and height can be controlled. The crimping of commercially-available Dacron vascular grafts (including both woven and knitted) was about one millimeter up and one millimeter down from the mean diameter of the grafts. Crimping as such can be achieved by this method for the bioresorbable grafts. The vascular graft is preferably coated with a bioresorbable biopolymer of this invention (especially the internal surface) to improve graft patency. The coating is usually an amorphous bioresorbable biopolymer or biopolymer blend which has some solubility in a solvent which is a non-solvent for the polymer or biopolymers forming the graft body. The coating may be applied to the graft by dissolving the coating biopolymer or biopolymer blend in a solvent which is a non-solvent for the graft polymer or biopolymer and then dipping the graft body into the solution.

Other preferred devices of this invention are those which are useful in ligament and tendon replacements. These devices are usually constructed of a fiber-like body composed of a relatively biodurable material such as graphite, polyethylene or a relatively longer lasting but bioresorbable biopolymer fiber of this invention and the like coated with one or more bioresorbable or biodegradable biopolymers. Organized tissue formation is encouraged by the use of the composites of this invention, which aids in regenerating ligaments and tendons.

Yet other preferred devices of the invention are those which are useful in dental and orthopedic repair. In this application, the dental and orthopedic repair devices may be used in composite structures with or without such materials as calcium hydroxyapatite, Bioglass, calcium triphosphate, drugs, and the like.

Still other preferred embodiments are devices for use as drug delivery system. Such drugs include drugs for control of body functions such as birth control and other medicinal drugs. In these embodiments, the drug can be dispersed in a bioresorbable biopolymer matrix having a bioresorption rate such that the desired quantity of drug is released into body as a function of time.

Other preferred devices of this invention are hollow fibers which are particularly suited for use as nerve channels for the repair of severed nerves. The diameters of the nerve channels will vary according to the size and shape of the nerve to be repaired. U.S. Pat. No. 3,833,002 discloses various sizes and shapes that may be employed. Lengths of the hollow fibers or tubes and their internal diameters and wall thicknesses will also vary according to intended use. The length of the hollow fiber or tube is usually sufficient to bridge the size of the gap to be repaired and to allow extra tubing in which to insert nerve stumps. Particularly useful internal diameters commonly range from about 0.13 mm to about 5.00 mm. Particularly useful wall thicknesses are usually from about 0.01 mm to about 3.0 mm, and preferably from about 0.05 mm to about 1.5 mm.

The preferred hollow fiber nerve channels may be formed from the biopolymers by any conventional technique such as solution dipping on a mandrel, melt extrusion, solution extrusion, gel extrusion, and the like. However, it is particularly useful to employ an extrusion process wherein the hollow fiber or tube dimensions may be carefully controlled by the extruding die dimensions, differential gas pressure between inner and outer surfaces of the tube, melt draw down and subsequent orientation process. Die dimensions are easily selected by consideration of the inner and outer diameters of the nerve channel, die swell, extrusion rates and orientation in the melt and rubbery state. For nerve channels having desired dimensions and evenness, the usual procedure is to pressurize the tube with an inert gas to prevent collapsing. The differential gas pressure is preferably maintained at about 0 to about 0.02 atm, most preferably 0 to about 0.004 atm. The melt draw down may be controlled by the ratio of average exit velocity out of the die and the take up velocity. The exit velocity for a given die and polymer melt viscosity is controlled by the extrusion pressure. Orientation is preferably effected by the ratio of speeds of two sets of rollers. Often a draw pin or heated surface is present between the rollers to stabilize the orientation process.

The devices of this invention are fabricated totally or in part from biopolymers having at least one type of recurring monomeric unit having the General Structures I or II:

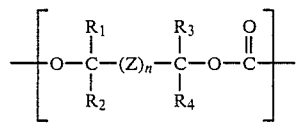

Structure I

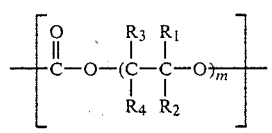

Structure II wherein Z, $R_1$, $R_2$, $R_3$, $R_4$, n and m are as described above.

Illustrative of useful $R_1$, $R_2$, $R_3$, and $R_4$ groups are hydrogen; alkyl such as methyl, ethyl, propyl, butyl, pentyl, octyl, nonyl, tert-butyl, neopentyl, isopropyl, sec-butyl, dodecyl and the like; cycloalkyl such as cyclohexyl, cyclopentyl, cyclooctyl, cycloheptyl and the like; alkoxyalkyl such as methoxymethylene, ethoxymethylene, butoxymethylene, propoxyethylene, pentoxybutylene and the like; aryloxyalkyl and aryloxyaryl such as phenoxyphenylene, phenoxymethylene and the like; and various substituted alkyl and aryl groups such as 4-dimethylaminobutyl, and the like;

Illustrative of other $R_1$ to $R_4$ groups are divalent aliphatic chains, which may optionally include one or more non-adjacent carbonyl, oxa, alkylaza, or arylaza groups such as $-(CH_2)_2-$, $-CH_2C(O)CH_2-$, $-(CH_2)_3-$, $-CH_2-CH(CH_3)-$, $-(CH_2)_4-$, $-(CH_2)_5-$, $-CH_2OCH_2-$, $-(CH_2)_2-N(CH_3)CH_2-$, $-CH_2C(O)CH_2-$, $-(CH_2)_2-N(CH_3)-(CH_2)_2-$, 1,4-cyclohexanediyl, 1,5-cyclooctanediyl, 1,3-cyclopentanediyl, 1,3-cyclohexanediyl, 2,2-dimethyl-1,5-cyclopentanediyl and the like, to form fused, spiro, bicyclic and/or tricyclic ring systems and the like.

Illustrative of useful $R_5$ and $R_6$ groups are the above-listed representative $R_1$ to $R_4$ groups, including $-OCH_2C(O)CH_2-$, $-(CH_2)_2-NH-$, $-OCH_2C(O)CH_2-$, and $-O-(CH_2)_2-O-$ and the like; alkoxy such as propoxy, butoxy, methoxy, isopropoxy, pentoxy, nonyloxy, ethoxy, octyloxy and the like; dialkylamino such as dimethylamino, methylethylamino, diethylamino, dibutylamino and the like; alkylcarbonyl such as acetyl, and the like; arylcarbonyl such as phenylcarbonyl, p-methylphenyl carbonyl and the like; and diarylamino and arylakylamino such as diphenylamino, methylphenylamino, ethylphenylamino and the like.

Preferred for use in the practice of this invention are devices formed totally or in part from homopolymers or copolymers formed from at least one type of recurring unit of the Structure I or Structure II wherein:

Z is $-[C(R_5R_6)]-$, $-O-$ or a combination thereof, where Z is selected such that there are no adjacent heteroatoms;

m is 1, 2, 3 or 4;

n is 1, 2 or 3; and $R_1$ to $R_6$ are as defined above, preferably where aliphatic moieties included in $R_1$ to $R_6$ include up to about 10 carbon atoms and aryl moieties include up to about 16 carbon atoms.

Illustrative of biopolymers for use in the fabrication of the preferred devices of this invention are those formed from at least one type of recurring monomeric unit of the Structure I wherein n is 1 and Z is of the formulas:

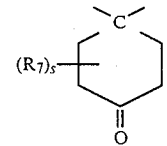

-continued

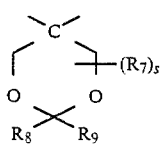

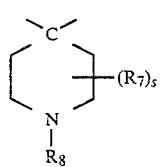

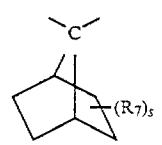

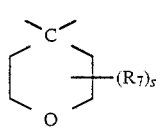

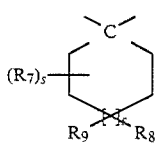

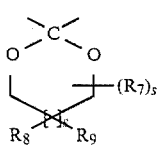

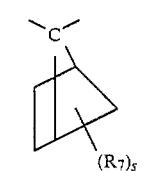

wherein:

—C— denotes the center carbon atom of Z, when Z is —[C(R$_5$R$_6$)]—;

R$_7$ is the same or different and is aryl, alkyl or an alkylene chain completing a 3 to 16 membered ring structure, including fused, spiro, bicyclic and/or tricyclic structures, and the like;

R$_8$ and R$_9$ are the same or different at each occurrence and are R$_7$ or hydrogen; and s is the same or different at each occurrence and is 0 to about 3, and the open valencies are substituted with hydrogen atoms.

Also illustrative of the preferred devices of this invention are those formed totally or in part from biopolymers comprising at least one type of recurring unit of the formula:

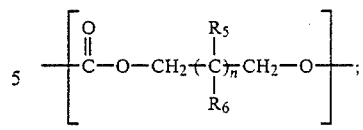

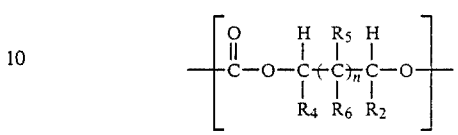

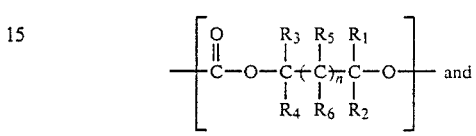

and

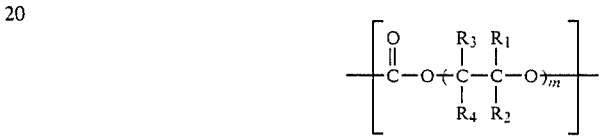

wherein:

R$_1$, R$_2$, R$_3$, and R$_4$ are the same or different at each occurrence and are hydrogen, alkyl such as methyl, ethyl, n-propyl, nonyl, isopropyl, n-butyl, sec-butyl, tert-butyl, neopentyl, and the like; phenyl; phenylalkyl, such as benzyl, phenethyl, and the like; phenyl substituted with one or more alkyl or alkoxy groups such as tolyl, xylyl, p-methoxyphenyl, m-ethoxyphenyl, p-propoxyphenyl, 1-methoxy-4-methylphenyl, and the like; and alkoxyalkyl such as methoxymethyl, ethoxymethyl and the like;

R$_5$ and R$_6$ are the same or different and are R$_1$ to R$_4$, alkoxy, alkanoyl, arylcarbonyl or dialkylamino; or R$_1$ to R$_6$ together may form alkylene chain completing 4, 5, 6, 7, 8 or 9 membered spiro, bicyclic and/or tricyclic ring structure, which structure may optionally include one or more non-adjacent divalent carbonyl, oxa, alkylaza or arylaza groups; with the proviso that when said biopolymer is a copolymer having recurring monomeric units of the Structure I derived from trimethylene carbonate the other recurring units of said copolymer are not derived from glycolic acid or glycolide.

n is 1, 2 or 3; and m is 1 to about 6:

Particularly preferred for use in the practice of this invention are devices fabricated totally or in part from biopolymers comprising at least one type of recurring unit of the formula:

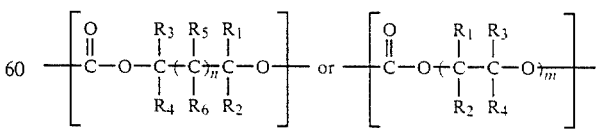

wherein:

R$_1$ to R$_4$ are the same or different and are alkyl, hydrogen, alkoxyalkyl, phenylalkyl, alkoxyphenyl or alkylphenyl, wherein the aliphatic moieties include from 1 to about 9 carbon atoms;

$R_5$ and $R_6$ are the same or different at each occurrence and are selected from the group consisting of $R_1$ to $R_4$ substituents, aryloxy, and alkoxy, or $R_5$ and $R_6$ together may form an aliphatic chain having from about 3 to about 10 membered spiro, bicyclic and/or tricyclic structure which may include one or two non-adjacent carbonyl, oxa, alkylaza or arylaza groups; with the proviso that when said biopolymer is a copolymer having recurring monomeric units of the Structure I derived from trimethylene carbonate the other recurring units of said copolymer are not derived from glycolic acid or glycolide.

n is 1 to about 3; and
m is 1 to about 6.

In the most preferred embodiments of this invention, the device is formed totally or in part from biopolymers comprising at least one type of recurring monomeric unit of the Structures II or III:

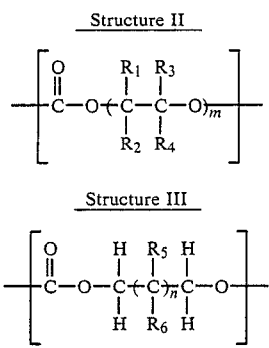

wherein:
n is 1 to about 3;
m is 1 to about 4;
$R_1$, $R_2$, $R_3$, $R_4$, $R_5$ and $R_6$ are the same or different and are hydrogen, aryl, alkylaryl, arylalkyl, or alkyl, or $R_5$ and $R_6$ together make a divalent chain forming about 3 to about 10 membered spiro, bicyclic, and/or tricyclic ring structure which may include one or two non-adjacent carbonyl, oxa, alkylaza or arylaza groups, with the proviso that when said biopolymer is a copolymer having recurring monomeric units of the Structure I derived from trimethylene carbonate, the other recurring units of said copolymer are not derived from glycolic acid or glycolide.

It is more preferred that the device is formed totally or in part of one or more biopolymers having at least one type or recurring monomeric unit of Structure II or III, where $R_1$ to $R_6$ are the same or different at each occurrence and are hydrogen, alkyl, alkylaryl, arylalkyl or aryl; or $R_5$ and $R_6$ together may form a divalent chain forming an about 3 to about 10 membered, preferably from about 5 to about 7 membered alicyclic, spiro and/or bicylic ring structure which may optionally include one or two non-adjacent oxa, carbonyl, alkylaza or arylaza functional groups. It is particularly preferred that the device be formed totally or in part of one or more of biopolymers having recurring unit of the Structure II or III in which $R_1$, $R_2$, $R_3$, $R_4$, $R_5$ and $R_6$ are the same or different and are hydrogen, aryl or alkyl, alkylaryl having from 7 to about 14 carbon atoms such as tolyl or phenyl; or lower alkyl of from 1 to about 7 carbon atoms such as methyl, ethyl, propyl, isopropyl, n-butyl, tert-butyl, pentyl, neopentyl, hexyl and sec-butyl.

In the most preferred embodiments of this invention, biopolymers used in the fabrication of the device has recurring unit of the Structures II or III, where n is 1, 2 or 3; m is 1 or 2 and $R_1$ to $R_6$ are the same or different and are hydrogen or lower alkyl having from about 1 to about 7 carbon atoms which do not differ from each other by more than about 3 carbon atoms, and preferably which do not differ by more than about 2 carbon atoms. In these embodiments, it is particularly preferred that $R_1$ to $R_4$ and $R_5$ to $R_6$ are the same and are hydrogen or alkyl of from about 1 to about 4 carbon atoms, n is 1, 2 or 3; and m is 1 or 2; and it is most preferred that $R_1$ to $R_6$ are methyl, ethyl or hydrogen; n is 1, 2 or 3; and m is 1 or 2.

The devices of this invention may be fabricated from one biopolymer or blends or composites may be used. Such blends and composites allow manipulations of various properties as for example bioresorption rate of the device, toughness of the device, pliability or elasticity of the device and the like.

The device of this invention may be fabricated from homopolymers having recurring units of Structures I and II. Alternatively, the device may be fabricated from block or random copolymers which including one or more types of recurring units of Structures I and/or II and at least one other type of recurring unit which may be bioresorbable or non-bioresorbable; or the device may be fabricated from random or block copolymers which include more than one type of recurring monomeric unit of Structure I or Structure II. Such copolymers can be random copolymers or may be block copolymers depending on the properties of the polymer required for the particular application. Illustrative of useful copolymers are random copolymers comprising one or more monomeric units of the Structures I or II and comprising one or more other types of bioresorbable monomeric units, as for example units derived from α-hydroxy carboxylic acids, dioxepanones, dioxanones, and the like, or one or more other types of recurring monomeric units of the Structure I and/or II. Also illustrative of copolymers useful in the fabrication of the device of this invention are block copolymers comprising one or more "A" blocks which may be formed of recurring units of Structures I and II, and one or more "B" blocks which may be formed from other types of bioresorbable recurring monomeric units, or which may be formed from one or more other types of recurring units of Structure I and II. Each "A" block and each "B" block may be the same or different. As used herein, the term "block" means a sequence of one type of monomeric unit at least about 5 monomeric units long, or such sequence of two or more types of recurring monomeric units either randomly distributed in such a sequence or distributed such sequence in a block-like fashion. Each "A" block and "B" block may comprise a single type of recurring monomeric unit. Alternatively, each block may comprise more than one type of recurring monomeric unit, randomly distributed throughout each block. For example, the block copolymers as described above may have repeating block units such as AB, ABA, BAB, ABAB, ABABA, BABAB, and the like, where each "A" block and each "B" block contains the same or substantially the same types of recurring monomeric unit, and/or where each block contains the same or substantially the same number of recurring units. Alternatively, the various "A" and "B" blocks contained in the block copolymers may have more than one type of "A" block or "B" block, each of which may contain a different type or types of recurring monomeric units; or each block may contain the same or different types of recurring units but have differing number of recurring units in each block. With respect to the recurring blocks of A's and B's, each of them may also be the same or different. For example, ABABA may in fact be MNOPQ, ABA may be MNQ or ABA may be MNOPQ, where M, N, O, P and Q are the same or different provided that at least one of M, N, O, P and Q is a recurring unit of the Structure I or II. Especially preferred are block copolymers of structures AB and ABA, with ABA being the most preferred.

In the preferred embodiment of this invention, the biopolymers of choice are copolymers; and block copolymers are especially preferred. Through use of selected monomeric units and their arrangement in the polymer chain, thermal history, mechanical processing and treatment of the biopolymers and the devices fabricated from the biopolymers, the properties of the biopolymer such as elasticity, modulus, pliability, hardness, softness and crystallinity, and the bioresorption rate of the biopolymers can be tailored and optimized for any particular application.

The other type of recurring monomeric units contained in the copolymers may vary widely and may be bioresorbable or nonbioresorbable. In the preferred embodiments of the invention the other types of recurring monomeric units are bioresorbable. Illustrative of the other type or types of recurring monomeric units are those which are derived from monomers which polymerize by ring opening polymerization as, for example, substituted and unsubstituted beta, gamma, delta, omega, and other lactones such as those of the formula:

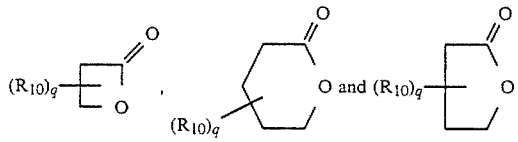

where $R_{10}$ is alkoxy, alkyl or aryl, and q is 0 to about 5, wherein the open valencies are substituted with hydrogen atoms. Such lactones include caprolactones, (d or l) 3-methylpropiolactone, (d or l) 3-ethyl-1-propiolactone, pivalolactone, valerolactones, butyrolactones, propiolactones and the lactones of hydroxy carboxylic acids such as 3-hydroxy-2-phenylpropanoic acid, 3-hydroxy-3-phenylpropanoic acid, 4-hydroxybutanoic acid, 3-hydroxybutanoic acid, 3-hydroxy-3-methylbutanoic acid, 4-hydroxypentanoic acid, 5-hydroxypentanoic acid, 3-hydroxy-4-methylheptanoic acid, 4-hydroxyoctanoic acid, and the like; and lactides such as l-lactide, d-lactide, and d,l-lactide; glycolide; and dilactones such as those of the formula:

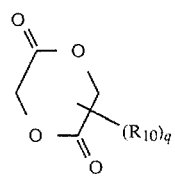

where $R_{10}$ and q are as defined above and where the open valencies are substituted with hydrogen atoms. Such dilactones include the dilactones of 2-hydroxycarboxylic acids such as 2-hydroxybutyric acid, 2-hydroxy-2-phenylpropanoic acid, 2-hydroxyl-3-methylbutanoic acid, 2-hydroxypentanoic acid, 2-hydroxy-4-methylpentanoic acid, 2-hydroxyhexanoic acid, 2-hydroxyoctanoic acid, and the like.

Illustrative of still other useful recurring units are those derived from dioxepanones such as those described in U.S. Pat. No. 4,052,988 and U.K. Pat. No. 1,273,733. Such dioxepanones include alkyl and aryl substituted and unsubstituted dioxepanones of the formula:

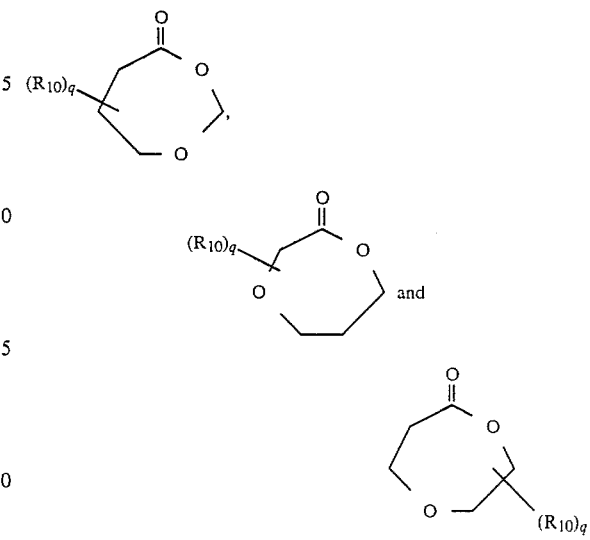

and monomeric units derived from dioxanones such as those described in U.S. Pat. Nos. 3,952,016, 4,052,988, 4,070,375, and 3,959,185, as for example, alkyl or aryl substituted and unsubstituted dioxanones of the formula:

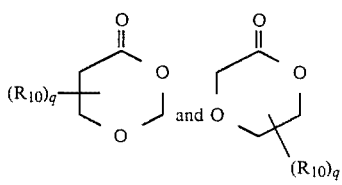

wherein q is as defined above; $R_{10}$ is the same or different at each occurrence and are hydrocarbyl groups such as alkyl and substituted alkyl, and aryl or substituted aryl; and the open valencies are substituted with hydrogen atoms. Preferably $R_{10}$ is the same or different and are alkyl groups containing from 1 to 6 carbon atoms, preferably 1 or 2 carbon atoms, and q is 0 or 1.

Suitable for use in such copolymers are monomeric units derived from ethers such as 2,4-dimethyl-1,3-dioxane, 1,3-dioxane, 1,4-dioxane, 2-methyl-5-methoxy-1,3-dioxane, 4-methyl-1,3-dioxane, 4-methyl-4-phenyl-1,3-dioxane, oxetane, tetrahydrofuran, tetrahydropyran, hexamethylene oxide, heptamethylene oxide, octamethylene oxide, nonamethylene oxide, and the like.

Also useful are monomeric units derived from epoxides such as ethylene oxide, propylene oxide, alkyl substituted ethylene oxides such as ethyl, propyl, and butyl substituted ethylene oxide, the oxides of various internal olefins such as the oxides of 2-butene, 2-pentene, 2-hexene, 3-hexene, and like epoxides. Still other useful monomeric units are those derived from epoxides/carbon dioxide such as ethylene oxide/$CO_2$ and its ethylene carbonate equivalent, and propylene oxide/$CO_2$ and its propylene carbonate equivalent; and monomeric units derived from orthoesters and orthocarbonates such as unsubstituted alkyl or aryl substituted orthoesters, orthocarbonates and cyclic anhydrides (which optionally include one or more oxa, alkylaza, arylaza, and carbonyl groups) of the formula:

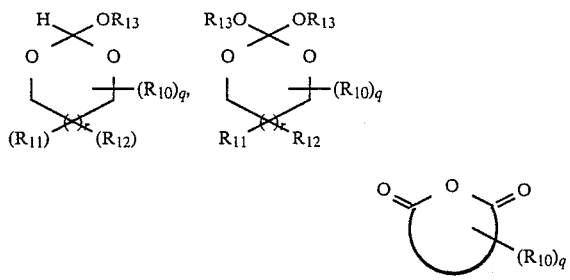

where q and $R_{10}$ are as described above, r is 0 to about 10, $R_{13}$ is the same or different at each occurrence and is alkyl or aryl, and $R_{11}$ and $R_{12}$ are the same or different and are hydrogen, alkyl or aryl.

Monomeric units derived from precursors and derivatives of lactides, lactones, dioxanones, orthoesters, orthocarbonates, anhydrides, and dioxepanones such as the various hydroxycarboxylic acids, substituted or non-substituted diacids such as oxa, aza, alkyl, aryl, substituted diacids, hydroxy substituted oxacarboxylic acids, functionalized esters, and acid halide derivatives, and the like can also be used other monomeric component of the copolymer.

Preferred copolymers used in fabricating the device of this invention are those which include two or more types of recurring monomeric units within the scope of Structures I and II, but those which include one or more types of recurring units of Structures I and II and one or more other types of bioresorbable recurring monomeric units derived from lactones, lactides and their precursors; orthoesters; dioxepanones; carbonates other than those of the Structures I and II; dioxanones; and orthocarbonates. Particularly preferred for use in the practice of this invention are copolymers comprising one or more types of recurring units of the Structures II or III, and one or more types of recurring monomeric units derived from gamma, delta and omega lactones and their precursor acids such as caprolactone, valerolactone, butyrolactone, 3-hydroxybutanoic acid, 4-hydroxybutanoic acid, propiolactone, (d or l) 3-methylpropiolactone and the like; lactides and their precursor acids such as l-lactide, d-lactide, d,l-lactide, 2-hydroxyisobutyric acid, 2-hydroxy-2-phenyl-propanoic acid, and the like; dioxepanones; dioxanones; carbonates other than those of the Structure I and II; orthoesters; and orthocarbonates. Other particularly preferred copolymers for use in the practice of this invention are those comprising two or more recurring units of the Structures II and III such as dimethyl-trimethylene carbonate/trimethylene carbonate copolymer.

Most preferred for use in the practice of this invention are random or block copolymers comprising one or more types of recurring monomeric units of the Structure III where $R_5$ and $R_6$ are the same or different and are hydrogen, methyl or ethyl and one or more other types of recurring monomeric units derived from lactones (preferably valerolactone, caprolactone, unsubstituted and alkyl substituted propiolactone and pivalolactone; lactides or their precursors; and carbonates other than those of the Structures I and II. Other most preferred devices of this invention are those formed totally or in part from block or random copolymers comprising two or more types of recurring monomeric units of the Structure III, in particular those having at least one type of recurring monomeric unit of the Structure III in which n is 1 and $R_5$ and $R_6$ are alkyl (such as units derived from dimethyltrimethylene carbonate), and at least one type of recurring monomeric unit of the Structure III in which n is 1 to about 3, and $R_5$ and $R_6$ are hydrogen, such as trimethylene carbonate, tetramethylene carbonate and pentamethylene carbonate.

The types of recurring monomeric units and molecular weight of the biopolymer, as well as the relative percentages of each of the recurring monomeric units in the copolymers used in the fabrication of the device of the invention may vary widely depending on the particular device and the desired characteristics of the copolymer or homopolymer. The types and quantities of recurring units and the molecular weight impact on the physical properties of the biopolymer such as tensile strength, modulus, hardness, elasticity, softness, toughness, compliancy, crystallinity, bioresorption rate and the like as needed for optimized or at least acceptable performance of the device. These properties, in turn, will be determinative of the characteristics of the device and the suitability and efficacy for use in any application. Various types and amounts of recurring monomeric units can be conveniently selected to tailor the properties of the copolymer to optimize the desirable properties required for any device.

While we do not wish to be bound by any theory, it is believed that whether it is random or block copolymer or a homopolymer, the higher the content of monomeric units of the Structure I or II wherein $R_1$ to $R_4$ are hydrogen, Z is $-[C(R_5R_6)]-$ wherein $R_5$ and $R_6$ are hydrogen; n is from 1 to 5; and m is from 1 to 5 the more flexible and soft the biopolymer will be. Conversely, in such random or block copolymers or homopolymers, the higher the content of monomeric units if the Structure II where m is 1 and $R_1$ to $R_4$ are hydrogen; and of the Structure I where $R_1$ to $R_4$ are hydrogen or alkyl, and Z is $[-C(R_5R_6]$ wherein $R_5$ and $R_6$ are the same and are alkyl or phenyl or $R_5$ and $R_6$ together form an alkylene chain which may optionally include one or more oxa groups completing a spiro ring structure the harder and more crystalline the biopolymer. For example, in those instances where a soft, pliable and relatively fast bioresorbing copolymer is required as for example as a coating on a Dacron vascular graft, monomeric units such as those of the Structure III where n is 1 to 3 and $R_5$ and $R_6$ are hydrogen are selected and are incorporated into the copolymer in a major amount. Similarly, soft and pliable coatings and devices can be obtained from a homopolymer of trimethylene carbonate, random copolymers of trimethylene carbonate and lactide (90:10), block copolymers of trimethylene carbonate and lactide (95:5), and random and block copolymers of dimethyl trimethylene carbonate and trimethylene carbonate (56:44).

In other situation where toughness and a slower bioresorption rate is desired as for example in a stent, a tendon or ligament replacement device, orthopedic plates and pins, monomeric units such as those of the Structure III where n is 1 and $R_5$ and $R_6$ are alkyl such as methyl are selected and incorporated into the copolymer in a major amount, and monomeric units, such as those of the Structure III where n is 1 and $R_5$ and $R_6$ are hydrogen in the minor amount. For example hard and crystalline devices can be obtained from a homopolymer of dimethyltrimethylene carbonate, or random copolymers of dimethyltrimethylene carbonate and trimethylene carbonate, dimethyltrimethylene carbonate/caprolactone, dimethyltrimethylene carbonate/tetramethylene carbonate and ABA block copolymers of dimethyltrimethylene carbonate/trimethylene carbonate/dimethyltrimethylene carbonate, dimethyltrimethylene carbonate/lactides/dimethyltrimethylene carbonate, dimethyltrimethylene carbonate/lactides, trimethylene carbonate/dimethyltrimethylene carbonate, and 1-lactide/trimethylene carbonate/1-lactide.

In general, in the preferred embodiments of this invention, recurring units of the Structure I, Structure II or Structure III are in the "major amount". As used herein, "major amount" is more than about 50 wt. % based on the total weight of all recurring monomeric units in the copolymer. In the preferred embodiments of the invention, the amount of recurring units of Structure I, Structure II and Structure III may range from greater than about 50 wt. % to about 100 wt. %, based on the total weight of recurring units in the copolymer, more preferably from about 80 wt. % to about 100 wt. %, and most preferably from about 85 wt. % to about 99 wt. %.

Useful average molecular weight ranges of biopolymers for use in any particular situation will vary depending on the desired characteristics of the biopolymer. In general, physical properties such as modulus, tensile strength, crystallinity and the like require a certain minimum molecular weight, which will vary with each biopolymer. Above this minimum, the properties do not depend strongly on molecular weight. Melt viscosity and solution viscosity increase with increasing molecular weight useful for a particular polymer. For this reason, there usually will be a maximum molecular practical weight because of the difficulty of processing it into the desired articles by conventional technology. Within the range of useful molecular weights, the rate of bioresorption will vary with the molecular weight and the crystallinity. Higher molecular weight and more crystalline or less crystalline biopolymers will require longer times to bioresorb than lower molecular weight biopolymers. The desired period of time over which the device will dictate the choice of molecular weight.

In general, the devices of this invention are formed totally or in part of biopolymers of the Structure I or II that can range in molecular weight from low molecular weight to extremely high molecular weight. Molecular weights of biopolymers for use in the practice of this invention usually are equal to or greater than about 5,000. Preferred average molecular weight ranges are from about 7,000 to about 5,000,000, with a range of from about 10,000 to about 500,000 being particularly preferred, and a range of from about 15,000 to about 250,000 being most preferred.

Other components may be combined with the biopolymers before they are formed into the devices of the invention, or added to, coated onto and the like, during or after their formation. These components include substances that will not interfere with the desired properties of the biopolymers, e.g., their ability to degrade into components biologically innocuous to living systems. Among the contemplated classes of such substances are placticizers, stabilizers for UV or temperature, pigments, lubricants and antioxidants. One of skill in the art will appreciate that any additives included in the medical devices of the invention, should be those that would meet with FDA approval.

Other optional polymeric components such as fibers, fillers and binders may be combined with the biopolymers prior to and during the formation the devices, or subsequent to their formation. These include, but are not limited to polymers and copolymers selected from the group consisting of polyesters such as poly(butylene terephthalate) and poly(ethylene terephthalate); poly(vinyl alcohol); poly(vinyl acetate) and partially hydrolyzed forms thereof; hydrogel type polymers such as poly(hydroxyethyl methacrylate), poly(hydroxypropyl methacrylate), and the like; polysulfones such as poly(phenylenesulfone); carbon; silicon carbide; halopolymers such as poly(tetrafluoroethylene), ethylene/tetrafluoroethylene copolymer; poly(dioxanone); poly(glycolide-co-trimethylene carbonates); poly(lactides); poly(d-lactide); poly(l-lactide); poly(lactide-co-caprolactone); poly(d,l-lactide); poly(caprolactones); poly(hydroxybutyrates); poly(hydroxyvalerates); poly(hydroxybutyrate-co-hydroxyvalerates); poly(glycolide); poly(urethanes); segmented poly(urethanes); poly(etherurethanes); poly(urethane ureas); silicone rubber; and substances such as fibrin and its powder; natural or processed collagen; mono-, di-, tri-, and poly (saccharides); poly(ethylenes); poly(amides); poly(propylene); peptides such as nerve growth factors, bone growth factors, laminin, and the like; poly(carbonates); poly(vinyl fluoride); poly(vinylidene fluoride); poly(vinyl butyral); cellulose such as, carboxylmethyl cellulose, cellulose acetate, ethylcellulose, and the like; ethylene vinylacetate copolymers and hydrolyzed and partially hydrolyzed forms thereof; poly(acrylonitrile); poly(vinyl methyl ether); and their derivative copolymers, blends, composites, and the like.

Other biocompatible components besides polymeric components may be combined with the polymers during or before they are formed into the devices of the invention, or added to, coated onto and the like, after their formation. These components include substances that will enhance certain of the desired properties of devices made from the biopolymers. Illustrative of such substances are plasticizers, lubricants, antioxidants, stabilizers of all kinds such as stabilizers for UV radiation, heat, moisture, and the like, as well as drugs for treatment of certain disorders or diseases and growth factors such as those for nerve and bone, and growth hormones in general. Materials such as calcium phosphate salts, ceramics, bioresorbable or otherwise, such as calcium hydroxyapatite, Bioglass, and calcium triphosphate may also be combined with the biopolymer. Components such as certain barium salts to render devices formed with them radio-opaque are also within the contemplation of the invention. Certain of these fillers, binders, additives and components can be removed or leached from such biopolymeric devices at some stage, so that a porous or semi-porous system can be obtained.

Devices of this invention may be fabricated totally from the biopolymers of the Structure I or II or may be fabricated in part from other bioresorbable materials or from biodurable materials which are relatively resistant to biodegradation. Illustrative of biodurable materials useful in the fabrication of devices of this invention are silicone, silicone rubber, poly(ethylene), poly(ethylene terephthalate), poly(fluoroethylenes), poly(phosphazene), poly(urethane), segmented poly(urethane), and the like. Also useful are biodurable metallic substances such as titanium, stainless steel, and alloys such as chrominium-cobalt-molybelenum alloys, titanium-aluminum-vanadium alloys, and the like.

The following are more specific examples of various embodiments of the invention and are not to be considered limitative thereof.

EXAMPLE 1

Synthesis of 5,5-Dimethyl-1,3-dioxan-2-one (Dimethyltrimethylene Carbonate (DMTMC))

A three liter three-necked round bottom flask was fitted with mechanical stirrer, 12 inch Vigreux column with distilling head and a thermometer. In the flask were placed 838 g (8.05 miles) 2,2-dimethyl-1,3-propanediol and 1098 mL (9.07 moles) diethyl carbonate. The mixture was immersed in an oil bath, heating initiated, and the stirrer started. By the time the temperature reached about 90° C., the diol had melted and dissolved in the carbonate. Powdered, dry sodium methoxide (21.6 g, 0.4 moles) was added through the neck used for the thermometer. The bath temperature was raised to 160° C.; ethanol began to distill out.

Over a period of about three hours, approximately 600 g (80% of theoretical) of distillate was collected; this is mainly ethanol with some diethyl carbonate. The reaction mixture gradually became very thick. Dry xylene (200 mL) was added through the top of the distilling column and the bath temperature was raised to 170°–180° C. Additional distillate was collected and the pot temperature gradually climbed to about 150° C.; when the distillation rate had slowed to only a few drops a minute, vacuum was cautiously applied to the system and gradually increased as the xylene and excess diethyl carbonate distilled out.

When the vacuum reached about 2–5 mm Hg, the product carbonate began to distill at about 125°–135° C. At this point, the vacuum was released with dry nitrogen and the oil bath lowered. The Vigreux column and distilling head were removed and replaced with a short path distillation head. Additional powdered sodium methoxide (5.4 g, 0.1 moles) was added quickly through the thermometer port.

Vacuum was applied to the system and adjusted to about 3–5 mm Hg. Heating was resumed and the product began to distill out. The bath temperature was raised to 210°–220° C. gradually in order to maintain the depolymerization rate of the oligomers to generate the product monomer. Care had to be taken not to rush the distillation, so that depolymerization of the dimer and oligomers could occur; otherwise, the dimer would have begun to distill over. Eventually, the pot residue became a gummy lump coated with powder and distillation ceased. Total yield of distillate was 852 g (81% of theory).

The product was a slightly sticky solid due to contamination with small amounts of impurities, such as xylene, diethyl carbonate, the starting diol and the cyclic dimer. It was recrystallized as follows. The total crude DMTMC (852 g) was dissolved in 430 mL tetrahydrofuran and 4.3 liters of anhydrous diethyl ether was added cautiously. The liquors were allowed to stand at room temperature for about one-half hour, then placed in a refrigerator at 4° C. overnight. The crystals were collected by filtration, washed with cold ether (1.2 liters), with hexane (1.2 liters), and then by pulling air through the filter cake for about one hour. Final drying was in a vacuum oven at 35°–40° C. (0.1 mm Hg). Total recovery of purified DMTMC was 730 g (70% overall yield).

EXAMPLE 2

Synthesis of 1,3-Dioxan-2-one (Trimethylene Carbonate (TMC))

A 1-liter three-neck round bottom flask was fitted with mechanical stirrer and a 12 in. Vigreux column topped with a distilling head having a stopcock for controlling the reflux ratio. The flask was charged with 1,3-propanediol (228.3 g, 3 mol) and diethyl carbonate (454 mL, 3.75 mol), flushed with nitrogen, then immersed in an oil bath. Heating was initiated and, when the temperature had reached about 80° C., sodium methoxide (1.62 g, 30 mmol) was added via funnel through the third neck. The oil temperature was raised to 155°–160° C., and ethanol soon began to reflux.

Ethanol was removed gradually over a period of about 3.5 hrs. under partial reflux. Takeoff cannot be too fast, as the temperature rises from about 80° C. as the distillate becomes rich in diethyl carbonate. A total of 268 grams of distillate was collected, with about 80–85% ethanol and the remainder carbonate by NMR. Additional sodium methoxide (0.40 g, 7.4 mmol) was cautiously added at this point and heating was continued for another 30 mins. A slight vacuum was carefully applied, and additional distillate collected. The vacuum was gradually increased until the pressure was down to about 1 mm, by which time most of the remaining diethyl carbonate was removed.

The oil bath was lowered and stirring continued for about 15 min. (temperature was not monitored). Triethylamine hydrochloride (5.2 g, 38 mmol) was added and stirring continued for 45 min. without heating. Stannous octoate (15 drops, about 0.2 grams) was added, heating resumed (bath at 150° C. initially, increasing to 200° C.), and a vacuum gradually applied to about 0.5 mm. An initial forecut boiling 70°–125° C. (25 g) was rejected, while the main fraction (245 g) collected at 125°–135° C. (0.5 mm) was about 85% pure by NMR. The residue from the distillation was dissolved in chloroform, filtered and distilled in a Kugelrohr at 160°–220° C. (0.1 mm) to give an additional 25 grams of dioxanone.

The main fraction was recrystallized from 1:1 ether:THF (4 mL/g) to give 168 g of dioxanone of high purity. Evaporation of the filtrate and trituration with ether-THF (about 4:1) gave an additional 45 g of crude product, which was combined with the 25 grams obtained from cracking of the residue. Recrystallization from ether-THF gave 46.5 g of pure dioxanone. The combined 214.5 grams of dioxanone was distilled in the Kugelrohr at 120°–130° C. (0.1 mm) to give 209.3 g (68% of theory) polymer grade product.

EXAMPLE 3

Polymerization of DMTMC

A freshly purified and dried sample of dimethyltrimethylene carbonate (12.1 g, 90 mmol) was loaded into a 15 mL polymerization tube. The tube was connected to a vacuum line via a rubber tubing and a stopcock, evacuated, and the DMTMC melted carefully with a heatgun. The tube was cooled in ice water, evacuated again, remelted, and cooled in ice. Vacuum was released with argon, the stopcock removed, and a solution of stannous octoate in toluene (100 μL of $3.0 \times 10^{-2}$M solution, 0.003 mmol) was added. The stopcock was reattached, the tube evacuated for several minutes to remove the toluene, then sealed with a torch. The contents of the tube were melted and thoroughly mixed, then the tube was immersed in an oil bath at 160° C. for 18 hours, cooled and broken. The polymer was dissolved in 250 mL chloroform, precipitated into 2 L of 2-propanol, washed with additional 2-propanol and dried in a vacuum oven at 50° C. The resulting powdery polymer (10 g, 83%) had a reduced viscosity of 3.0 dL/g (0.1% solution in dioxane).

EXAMPLE 4

Poly(TMC)

A freshly distilled sample of trimethylene carbonate (10.9 g, 107 mmol) was melted in a round bottom flask under argon and transferred via syringe into a 15 mL polymerization tube. The tube was connected to a vacuum line via rubber tubing and a stopcock and evacuated. The tube was cooled in ice water, evacuated again, remelted, and cooled in ice. Vacuum was released with argon, the stopcock removed, and a solution of stannous octoate in toluene (250 μL of $1.3 \times 10^{-2}$M, 0.003 mmol) was added. The stopcock was reattached, the tube evacuated for several minutes to remove the toluene, then sealed with a torch. The contents of the tube were melted and thoroughly mixed, then the tube was immersed in an oil bath at 160° C. for 18 hrs, cooled and broken. The polymer was dissolved in 250 mL chloroform, precipitated into 2 L of 2-propanol, washed with additional 2-propanol and dried in a vacuum oven at 50° C. The resulting rubbery polymer (10 g, 83%) had a reduced viscosity of 2.13 dL/g (0.1% solution in dioxane). GPC analysis versus polystyrene standards gave an approximate weight average molecular weight of 91,000.

EXAMPLE 5

Fiber Spinning

The DMTMC homopolymer of Example 3 was melt spun at 160° C. into a 70 denier filament. The material appears to crystallize very rapidly. Sections of yarn were hand drawn to approximately 30 denier and tested. Satisfactory fiber properties for fabric and hollow fiber applications were achieved. Fiber properties are: Denier (55); Tensile Modulus (59 grams/denier); Tensile Strength (3 grams/denier); Ultimate Elongation (26%).

EXAMPLE 6

Poly (TMC-co-1-Lactide)

Freshly distilled trimethylene carbonate (12.95 g, 127 mmol) was melted together with dried, recrystallized l-lactide (2.03 g, 14.1 mmol), then the mixture was syringed into a 15 mL polymerization tube. The catalyst (73 μL of $3.0 \times 10^{-2}$M stannous octoate in toluene) was added, then the tube was degassed by freezing, pumping and thawing twice. After sealing under vacuum, the tube was immersed in an oil bath at 160° C. for 60 hours. The tube was cracked and 10 g of the crude polymer was dissolved in chloroform (250 mL), then precipitated into isopropanol. The dried polymer, 8.6 g, had a reduced viscosity of 1.53 dL/g (0.1% solution in dioxane).

In another experiment, freshly distilled trimethylene carbonate (12.95 g), 2.03 grams of recrystallized L-lactide and 7.5 μl of 1.0M stannous octoate in toluene was placed inside a 160° C. oil bath for 16 hrs. The ampule was cracked and 12.9 grams was the final yield after twice reprecipitated from tetrahydrofuran (THF) solution. The weight average molecular weight was 87,000 and number average molecular weight was 13,760 by GPC in THF. The GPC system was calibrated with polystyrene standards.

EXAMPLE 7

Copolymerization in sealed tube of DMTMC and Trimethylene Carbonate (TMC), 97.5:2.5

A mixture of freshly purified and dried DMTMC (14.64 g, 112.5 mmol), TMC (378 mg, 3.7 mmol), and 2,2-dimethylpropanediol (12 mg, 0.116 mmol) was combined in a polymerization tube, evacuated, and the tube filled with argon. Stannous octoate (65 μL of $3 \times 10^{-2}$M solution in toluene) was added and the tube evacuated for several minutes. The tube was sealed with a torch, the contents melted and thoroughly mixed, then immersed in an oil bath at 160° C. overnight. After chilling in liquid nitrogen, the tube was broken, the contents were dissolved in dioxane (250 mL), and precipitated into 1 L of ice water. The polymer was washed with water (2×500 mL) and dried in vacuo overnight at 50° C. Yield: 13.1 g (87%); reduced viscosity 0.68 dL/g (0.1% in dioxane). [Sample 9, Table I]

EXAMPLE 8

Copolymerization in resin flask of DMTMC and TMC, 97.5:2.5

An oven-dried, silanized glass 150 mL resin flask was equipped with mechanical stirrer and a teflon paddle, argon inlet, a serum cap on one port, and a glass stopper on the remaining port. To the flask were added freshly dried and purified DMTMC (29.25 g, 225 mmol), TMC (0.75 g, 7.4 mmol), and dimethylpropanediol (12 mg, 0.12 mmol). The flask was evacuated and filled with argon several times, then immersed in an oil bath at 120° C. to melt the monomers. The temperature was raised to 145° C. in 10 minutes, then 125 μL of a $3 \times 10^{-2}$M solution of stannous octoate in toluene was added. The temperature was raised to 160° C. in another 10 minutes. Within another 10 minutes the material had become very thick and after one hour the reaction was stopped, the polymer was dissolved in chloroform and precipitated into 2-propanol. Yield: 24.4 g, (81%); reduced viscosity 0.80 dL/g (0.1% in dioxane). [Sample 10, Table I].

EXAMPLE 9

Poly(DMTMC co TMC), 97.5:2.5

A polymerization was carried out as in the preceding example, with the following changes. The resin kettle was of 1 L capacity; 292.5 g DMTMC, 7.5 g TMC and 105 mg dimethylpropanediol were used. Initial heating was at 140° C. and the catalyst was 160 μL of 1.0M stannous octoate in toluene. After 4 hours a total of 277 g of polymer was isolated from the flask; gel permeation chromatography (GPC) using THF showed a weight average molecular weight of 89,000 and a dispersity of 2.4 for the polymer peak, plus small amounts of oligomers. For spinning into fibers, the polymer was dissolved in dioxane and precipitated into water. [Sample 22, Table I]

EXAMPLE 10

Copolymerization of DMTMC and Caprolactone, 98.2:1.8

A mixture of DMTMC (26.34 g, 202 mmol), freshly distilled caprolactone (0.475 mL, 0.489 g (4.3 mmol), 2,2-dimethyl-1,3-propanediol (0.2 mmol) and stannous octoate (150 µL of 0.1M solution in toluene) was divided between three polymerization tubes. The tubes were sealed under vacuum and heated at 160° C. overnight. The resulting polymers were combined, dissolved in tetrahydrofuran and precipitated into water. Yield: 38.8 g (87%). Weight average molecular weight=89,000 by GPC (THF). [Sample 29, Table II]

EXAMPLE 11

Poly(DMTMC co Caprolactone)

In an oven-dried, silanized 1 L resin flask were combined DMTMC (313.7 g, 2.41 mol), distilled caprolactone (5.62 g, 49 mmol) and 2,2-dimethyl-1,3-propanediol (63 mg, 0.60 mmol). After purging with argon the flask was heated to 160° C. in an oil bath; when the mixture had become homogeneous, stannous octoate (155 µL of a 1.0M solution in toluene) was added. The mixture gradually became very thick; stirring was discontinued after 2.5 h and the reaction was stopped after an additional 3.5 h. The polymer was combined with those from two smaller runs, dissolved in tetrahydrofuran and precipitated into water. Yield: 650 g (92%). Weight average molecular weight=89,300 by GPC (THF). [Sample 30, Table II]

EXAMPLE 12

A series of copolymers of DMTMC with varying amounts of TMC (Tables I, III) and lactides, or caprolactone (Tables II, III) were evaluated. Certain of these were spun into approximately 70 denier filament. These polycarbonate copolymers could be melt spun easily in the temperature range 150° to 190° C. with good melt stability as indicated at a constant melt viscosity. Drawn samples, e.g., 4A and 4B (Table III), showed satisfactory fiber tensile strength properties for fabric and hollow fiber or tubular applications as nerve channels.

EXAMPLE 13

A higher molecular weight polycarbonate resin with reduced viscosity 1.1 of DMTMC and TMC (97.5:2.5) was extruded similarly as Example 12, but with a melt temperature of 195° C. The 0.030 inch die used had an exit melt velocity of 0.3 ft/min. and taken up at about 30 ft/min. The fibers continued on to a set of draw godets and are subjected to increase in draw ratio. The test results, 15A to 15E (Table III), show good fiber properties for many fabric and hollow tube applications.

EXAMPLE 14

A copolymer of DMTMC and caprolactone of 98.2:1.8 weight ratio (Sample 29, Table II) was spun as in Example 12. Fibers from a number of draw ratios showed good tensile and hollow fiber or tube properties (see Example 29 A–D in Table III).

EXAMPLE 15

A sample of a 300 g batch of a copolymer of DMTMC with TMC (97.5 to 2.5 wt. %) was prepared to provide information on conditions for spinning multifilament yarn. The material was melt spun as in Example 12 using a melt temperature of 180° C. The fibers were then drawn to yield tensile properties listed in Table III as Sample 22. Satisfactory properties for fabric and hollow fiber or tubing applications are indicated.

EXAMPLE 16

Polycarbonate polymer recovered from Example 15 dissolved and reprecipitated was melt spun at 180° C. with a lower melt draw down and oriented to give satisfactory fiber properties listed as Sample 22A in Table III.

TABLE I

RANDOM COPOLYMERS OF DMTMC (D) AND TMC (T)

| Sample Number | D:T Weight Ratio | Method of Synthesis | Quantity Isolated | Yield (%) | Reduced Viscosity |
|---|---|---|---|---|---|
| 1 | 95:5 | Example 7 | 11.3 g | 79 | 0.76 |
| 2 | 95:5 | Example 7 | 9.3 g | 62 | 0.77 |
| 3 | 97.5:2.5 | Example 7 | 11.9 g | 83 | 0.66 |
| 4 | 97.5:2.5 | Example 7 | 24.0 g | 82 | 0.53 |
| 5 | 97.5:2.5 | Example 7 | 24.3 g | 82 | 0.57 |
| 6 | 97.5:2.5 | Example 7 | 24.0 g | 80 | 0.71 |
| 7 | 97.5:2.5 | Example 7 | 37.5 g | 82 | 4.9 |
| 8 | 97.5:2.5 | Example 7 | 48.5 g | 83 | 5.6 |
| 9 | 97.5:2.5 | Example 7 | 13.1 g | 87 | 0.68 |
| 10 | 97.5:2.5 | Example 8 | 24.4 g | 81 | 0.80 |
| 11 | 97.5:2.5 | Example 7 | 26.6 g | 89 | 0.83 |
| 12 | 25:75 | Example 7 | 7.8 g | 89 | 0.86 |
| 13 | 97.5:2.5 | Example 8 | 25.0 g | 83 | 0.38 |
| 14 | 97.5:2.5 | Example 7 | 10.4 g | 87 | 1.46 |
| 15 | 97.5:2.5 | Example 7 | 10.4 g | 87 | 1.10 |
| 16 | 97.5:2.5 | Example 8 | 5.1 g | 85 | 0.91 |
| 17 | 97.5:2.5 | Example 7 | 5.3 g | 88 | 1.30 |
| 18 | 97.5:2.5 | Example 9 | 90.0 g | 90 | 0.43 |
| 19 | 97.5:2.5 | Example 7 | 8.3 g | 83 | |
| 20 | 97.5:2.5 | Example 9 | 90.0 g | 90 | |
| 21 | 97.5:2.5 | Example 9 | 282 g | 94 | |
| 22 | 97.5:2.5 | Example 9 | 277 g | 92 | |
| 23 | 97.5:2.5 | Example 9 | 291 g | 97 | |
| 24 | 96.8:3.2 | Example 7 | 9.8 g | 94 | |
| 25 | 56.0:44 | Example 7 | 8.6 g | 87 | |
| 26 | 30.0:70 | Example 7 | 6.6 g | 73 | |
| 27 | 79:0:21 | Example 7 | 6.4 g | 94 | |

| Sample Number | GPC Main Wt Av MW | Peak Disp. | GPC Overall Wt Av MW | Disp. |
|---|---|---|---|---|
| 1 | | | | |
| 2 | | | | |
| 3 | | | | |
| 4 | | | | |
| 5 | | | | |
| 6 | | | | |
| 7 | | | | |
| 8 | | | | |
| 9 | | | | |
| 10 | | | | |
| 11 | | | | |
| 12 | | | | |
| 13 | | | | |
| 14 | | | 150,000 | 18.80 |
| 15 | | | 115,000 | 7.93 |
| 16 | 64,300 | 3.10 | 62,000 | 10.20 |
| 17 | | | | |
| 18 | 35,100 | 4.00 | | |
| 19 | 62,500 | 2.88 | 80,500 | 13.40 |
| 20 | 85,600 | 4.36 | 86,700 | 29.30 |
| 21 | 142,000 | 3.57 | 127,000 | 37.60 |
| 22 | 88,700 | 2.38 | 82,500 | 17.80 |
| 23 | 113,000 | 3.60 | 108,000 | 18.40 |
| 24 | 257,000 | 3.48 | 257,000 | 28.20 |
| 25 | 148,000 | 2.06 | 148,600 | 2.07 |
| 26 | 41,800 | 2.00 | 41,800 | 2.01 |
| 27 | 202,360 | 3.16 | 219,000 | 34.60 |

TABLE II

RANDOM COPOLYMERS OF DMTMC (D)/ CAPROLACTONE (CL) AND DMTMC (D)/d,1-LACTIDE

| Sample Number | D:CL Ratio | Method of Synthesis | Quantity Isolated | Yield (%) |
|---|---|---|---|---|
| 27 | 98.2:1.8 | Example 11 | 54.3 g | 84 |
| 28 | 98.2:1.8 | Example 11 | 62.0 g | 95 |
| 29 | 98.2:1.8 | Example 10 | 38.8 g | 87 |
| 30 | 98.2:1.8 | Example 11 | 650 g | 92 |
| 31 | 95.6:4.4 | Example 10 | 9.4 g | 95 |
| 32 | 77.4:22.6 | Example 10 | 9.6 g | 96 |
| 33 | 53.3:46.7 | Example 10 | 8.8 g | 93 |
| 34 | 91.1:8.9 | Example 10 | 8.3 g | 88 |
| 35 | 87.8:12.2* | Example 10 | 8.6 g | 86 |

| Sample Number | GPC Main Peak Wt Av MW | Disp. | GPC Overall Wt Av MW | Disp. |
|---|---|---|---|---|
| 27 | 46,500 | 2.03 | | |
| 28 | 124,000 | 2.50 | 150,000 | 16.30 |
| 29 | 99,500 | 1.34 | 89,000 | 29.53 |
| 30 | 91,500 | 2.42 | 89,300 | 4.79 |
| 31 | 132,000 | 2.36 | 156,000 | 11.50 |
| 32 | 104,000 | 1.63 | 170,200 | 2.85 |
| 33 | 14,800 | 2.06 | 14,900 | 2.07 |
| 34 | 10,100 | 2.39 | 88,900 | 29.50 |
| 35 | 88,900 | 2.54 | 87,000 | 6.65 |

*87.8 = D:12.2 = d,1-Lactide

General Procedures for Large Scale Biopolymer Spinning

Random copolymers of these biopolymers such as DMTMC/TMC and DMTMC/CL were spun using the following equipment and procedures:

Dry polymer was charged into a hopper of a Braebender ¾ inch extruder equipped with two adjustable electrically heated zones and a heated block assembly consisting of an electrically heated metal block and No. 2 Zenith gear pump. The spinnerette consisted of a stainless steel (316) die, containing 8 holes, 0.021" diameter and a 200 mesh screen pack.

Feed rate, extrusion temperatures and pressures are presented in Examples 17 and 18.

The filaments were air quenched and taken up on a constant speed godet set at 1448 ft/min. The second godet was set at 2854 ft/min. which resulted in a draw ratio of 2:1. Yarn haul off was made using a Leesona winder.

EXAMPLE 17

Run Parameters

Material: 97.5% DMTMC—2.5% TMC, Random copolymer, Samples 21–23 (Table I).
Extruder: ¾" Braebenders
Heat:
Zone 1 (feed) 200° C.
Zone 2 (metering) 212° C.
Zone 3 (die and block) 215° C.
Screen Pack 200 mesh
Die 8 hole 0.021" diameter
Screw RPM 6
Pump RPM in percent 22
Pressure barrel 1200 psi
Pressure die 600 psi
Take up:
  Roll 1/temperature 1448 ft/min. at R.T.
  Roll 2/temperature 2854 ft/min. at R.T.
Final thruput 0.4 gms/hole/min.
Final draw ratio 2:1
Denier 5 DPF towed to 200/40

EXAMPLE 18

Run Parameters

Material: 98.2% DMTMC—1.8% CL, Random copolymer, Sample 30 (Table II)
Extruder: ¾" Braebender
Heat:
Zone 1 (feed) 190° C.
Zone 2 (metering) 200° C.
Zone 3 (die and block) 210° C.
Screen Pack 200 mesh
Die 8 hole 0.021" diameter
Screw RPM ~6
Pump RPM in percent ~22
Pressure barrel 1200 psi
Pressure die 600 psi
Take up:
  Roll 1/temperature 1448 ft/min. at R.T.
  Roll 2/temperature 2854 ft/min. at R.T.
Final thruput 0.4 gms/hole/min.
Final draw ratio 2:1
Denier 5 DPF towed to 200/40

TABLE III

Fiber Mechanical Properties

| Sample | Denier | Tensile Modulus (g/d) | Tensile Strength (g/d) | Ultimate Elongation (%) |
|---|---|---|---|---|
| 4A | 10 | 90 | 5.5 | 16 |
| 4B | 13 | 70 | 3.4 | 24 |
| 10 | 198 | 22 | 0.3 | 7 |
| 15A | 33 | 37 | 1.4 | 24 |
| 15B | 19 | 41 | 1.5 | 29 |
| 15C | 17 | 51 | 2.5 | 26 |
| 15D | 17 | 57 | 2.7 | 23 |
| 15E | 4 | 82 | 4.0 | 17 |
| 29A | 13 | 45 | 3.4 | 50 |
| 29B | 13 | 43 | 3.7 | 53 |
| 29C | 13 | 50 | 3.7 | 49 |
| 29D | 11 | 88 | 4.4 | 20 |
| 22 | 12 | 62 | 4.5 | 27 |
| 22A | 48 | 45 | 4.8 | 30 |
| 24 | 29 | 43 | 2.9 | 43 |

EXAMPLE 19

Copolymerization of DMTMC and TMC in Xylene Solution

In an oven-dried 100 mL resin flask DMTMC (7.81 g, 60 mmol), TMC (6.13 g, 60 mmol) and dimethylpropanediol (3 mg) were combined. The flask was evacuated to 0.1 mm Hg for ten minutes, then filled with dry argon. Xylene (15 mL), dried by distilling from sodium metal, was added to the flask by syringe, then the flask was immersed in an oil bath at 150° C. After stirring for five minutes, tin octoate (25 μL of a 1.0M solution in toluene) was added. The solution became very viscous over a two hour period; a sample (ca. 200 mg) was taken and diluted with 5 mL tetrahydrofuran. Analysis by GPC showed a weight average molecular weight of 142,000. The polymer solution was precipitated into methanol, the polymer washed with methanol and dried. NMR analysis of the precipitated sample showed a TMC content of 51% and DMTMC content of 49%. From the carbonyl carbon region of the 100 MHz carbon spectrum, it was determined that the carbonate groups of the polymer consisted of 27% DMTMC-DMTMC linkages, 28% TMC-TMC linkages and 45% DMTMC-TMC linkages.

EXAMPLE 20

ABA Block copolymer of
5,5-Dimethyl-1,3-dioxan-2-one (DMTMC) and
Caprolactone (CL); B=1:1 DMTMC:CL,
A=DMTMC, A:B=80:20

An oven-dried, silanized glass 150 mL resin flask was equipped with mechanical stirrer and a teflon paddle, argon inlet, a serum cap on one port, and a glass stopper on the remaining port. To the flask were added freshly dried and purified DMTMC (4.15 g, 31.9 mmol), caprolactone (3.64 g, 31.9 mmol), and 2,2-dimethylpropanediol (7.5 mg, 0.072 mmol). The flask was evacuated and filled with argon several times, then immersed in an oil bath at 160° C. Stirring was initiated, and after 5 minutes, 25 µL of a 1.0M solution of stannous octoate in toluene, the catalyst solution, was added. Noticeable thickening occurred in about 20 minutes; after 1.5 hours, the oil bath was lowered and the flask was evacuated briefly to remove some of the unreacted monomers that had condensed on the upper part of the flask. Heating was resumed and DMTMC (6.64 g, 51 mmol) was added, followed by an additional 25 µL of the catalyst solution. After an additional 10 minutes, more DMTMC (26.57 g, 204.2 mmol) was added and the mixture stirred with continued heating at 160° C. In about 30 minutes, the mixture became too thick to be stirred, but heating was continued for an additional hour, when the polymerization was terminated.

The viscous polymer was scooped out of the flask (37.8 g recovery), dissolved in dioxane (300 mL), and precipitated in a blender into water (1200 mL). The polymer was then washed twice in the blender with water, filtered and dried in vacuum at 45° C. overnight. Yield: 32.9 g (80%). Weight average molecular weight=121,000 by GPC (THF solvent). [Sample 3, Table IV]

EXAMPLE 21

ABA Block Copolymer of DMTMC and Caprolactone (CL); B=1:1 DMTMC:CL, A=DMTMC, A:B=70:30

A polymerization similar to Example 20 was carried out in a 1 liter resin flask. The first (B-block) stage employed 39.04 g (300 mmol) DMTMC, 34.24 g (300 mmol) caprolactone, 30 mg (0.29 mmol) 2,2-dimethylpropanediol, and 150 µL of 1M stannous octoate in toluene. After 2 hours heating at 160° C., the reactor was evacuated briefly and all of the remaining DMTMC (182.2 g, 1400 mmol) was added at once. An additional 150 µL of catalyst solution was added and stirring continued for 2.5 hours until the polymer became too viscous to stir. Heating at 160° C. was continued overnight, then the polymer was removed from the flask, dissolved in 2.5L dioxane and precipitated in batched into water (ca 10L). After washing and drying as before, the polymer weighed 226 g (89%). Weight average molecular weight=110,000 by GPC (THF); caprolactone content by $^1$H NMR=17% (theory 15%). [Sample 8, Table IV]

Similarly, other examples of these block copolymers of DMTMC and caprolactone were prepared and reported in Table IV.

EXAMPLE 22

ABA Block Copolymer of DMTMC and Trimethylene Carbonate (TMC); B=TMC, A=DMTMC, A:B=80:20

A polymer was prepared as in Example 20, except that the initial charge consisted of TMC (6.12 g, 60 mmol) and 2,2-dimethylpropanediol (10.3 mg, 0.1 mmol). The flask was immersed in an oil bath at 160° C., then after five minutes 25 µL of 1M stannous octoate was added. In 30 minutes the TMC had polymerized to a viscous material; this was sampled and then DMTMC (31.12 g, 240 mmol) was added all at once. The poly(TMC) prepolymer gradually dissolved in the DMTMC and the mixture became homogeneous and eventually very viscous. After a total time of 3.5 hours, the reaction was stopped and worked up as in Example 20. Yield: 27.7 g (74%). Trimethylene carbonate content by $^1$H NMR=23.6% (theory 20%). Weight average molecular weight by GPC (THF) of prepolymer=37,000, of final polymer=105,000. Differential scanning calorimetry (DSC) of the final polymer showed a glass transition temperature (Tg) of 0° C. and a melting temperature (Tm) of 71° C. [Sample 20, Table V].

Similarly, other examples of such block copolymers of DMTMC and TMC or DMTMC and TMC/lactides were prepared and reported in Table V.

EXAMPLE 23

Block Copolymerization of DMTMC and TMC in Xylene Solution

In an oven-dried 100 mL resin flask were combined DMTMC (7.81 g, 60 mmol), TMC (6.13 g, 60 mmol) and dimethylpropanediol (3 mg). The flask was evacuated to 0.1 mm Hg for ten minutes, then filled with dry argon. Xylene (15 mL), dried by distilling from sodium metal, was added to the flask by syringe, then the flask was immersed in an oil bath at 150° C. After stirring for five minutes, tin octoate (25 µL of a 1.0M solution in toluene) was added. The solution became very viscous over a two hour period; a sample (ca. 200 mg.) was taken and diluted with 5 mL THF. Analysis by GPC showed a weight average molecular weight of 142,000. The solution was precipitated into methanol. The polymer was washed with methanol and dried. NMR analysis of the precipitated sample showed a TMC content of 51% and DMTMC content of 49%. From the carbonyl carbon region of the 100 MHz carbon spectum, it was determined that the carbonate groups of the polymer consisted of 27% DMTMC-DMTMC linkages, 28% TMC-TMC linkages and 45% DMTMC-TMC linkages.

Additional DMTMC (10.41 g, 80 mmol) was added to the flask and the mixture stirred at 150° C. for an additional 3.5 hours. The polymer was dissolved in 350 mL dioxane, precipitated into methanol (1100 mL), washed with additional methanol and dried. Yield: 19.0 g (78%). Weight average molecular weight=168,000 by GPC (THF). TMC content=32% by proton NMR (theory=30%). The carbonyl region of the spectrum shows 48% DMTMC-DMTMC linkages, 36% DMTMC-TMC linkages and 16% TMC-TMC linkages; calculated values assuming only DMTMC-DMTMC linkages are formed in the second stage: 50% DMTMC-DMTMC, 31% DMTMC-TMC, and 19% TMC-TMC.

EXAMPLE 24

The block copolymer of DMTMC and caprolactone listed as Sample 2 in Table IV was melt extruded into monofilament fiber at 195° C. The fibers were drawn at room temperature and good fiber characteristics were obtained as documented in Table VI as samples 2A–2G.

EXAMPLE 25

The block copolymer of DMTMC and caprolactone listed as Sample 3 in Table IV was melt extruded and moderately drawn to limit the tensile modulus. Low modulus fibers of good strength and high elongations were achieved as shown in Table VI as entries 3A–3B.

EXAMPLE 26

The block copolymer of DMTMC and caprolactone listed as Sample 5 in Table IV was melt spun and drawn at room temperature at a number of low draw ratios to limit the modulus. Good fiber strengths at these low moduli were achieved as shown in Table VI as 5A–5E.

EXAMPLE 27

Fiber 5D from Table VI was heat set on a heated block at 74°–77° C. at 100 ft/min under a 2% overdraft and at draw ratios of 1.06, 1.22, 1.3 and 1.42. These fibers are listed as 5D-1 through 5D-5, respectively, in Table VI.

TABLE IV
ABA BLOCK COPOLYMERS OF CAPROLACTONE (CL) AND DIMETHYLTRIMETHYLENE CARBONATE (DMTMC)

| Sample Number | A Block | B Block | A:B Ratio | Quantity Isolated | Yield (%) |
|---|---|---|---|---|---|
| 1 | DMTMC | DMTMC:CL 3:1 | 70:30 | 20.0 g | 65 |
| 2 | DMTMC | DMTMC:CL 4:1 | 85:15 | 41.3 g | 87 |
| 3 | DMTMC | DMTMC:CL 1:1 | 80:20 | 32.9 g | 80 |
| 4 | DMTMC | DMTMC:CL 3:1 | 77:23 | 33.4 g | 81 |
| 5 | DMTMC | DMTMC:CL 1:1 | 70:30 | 32.1 g | 79 |
| 6 | DMTMC | DMTMC:CL 1:1 | 70:30 | 210.4 g | 82 |
| 7 | DMTMC | DMTMC:CL 1:1 | 70:30 | 223.7 g | 88 |
| 8 | DMTMC | DMTMC:CL 1:1 | 70:30 | 226.6 g | 89 |
| 9 | DMTMC | DMTMC:CL 1:1 | 70:30 | Blended | |

| Sample Number | GPC Main Wt Av MW | Peak Disp. | GPC Overall Wt Av MW | Disp. |
|---|---|---|---|---|
| 1 | 47,300 | 2.55 | 50,400 | 4.63 |
| 2 | 118,000 | 3.70 | 181,000 | 47.60 |
| 3 | 140,000 | 4.20 | 121,000 | 33.60 |
| 4 | 92,000 | 3.50 | 93,400 | 13.15 |
| 5 | 132,000 | 2.80 | 152,000 | 14.30 |
| 6 | 67,100 | 1.90 | 67,100 | 1.90 |
| 7 | 83,800 | 1.68 | 83,800 | 1.68 |
| 8 | 110,000 | 2.90 | 113,000 | 19.50 |
| 9 | 89,600 | 2.90 | 112,500 | 16.50 |

TABLE V
ABA BLOCK COPOLYMERS OF TRIMETHYLENE CARBONATE (TMC), d,l-lactic acid(LA) AND DIMETHYLTRIMETHYLENE CARBONATE (DMTMC)

| Sample Number | A Block | B Block | A:B Ratio | Quantity Isolated | Yield (%) |
|---|---|---|---|---|---|
| 10 | DMTMC | TMC:DMTMC 1:1 | 25:75 | 33.6 g | 88 |
| 11 | DMTMC | TMC:DMTMC 1:1 | 35:65 | 33.4 g | 75 |
| 12* | DMTMC | TMC:DMTMC 1:1 | 65:35 | 35.8 g | 80 |
| 13 | DMTMC | TMC:DMTMC 1:1 | 40:60 | 36.0 g | 82 |
| 14 | DMTMC | TMC:DMTMC 1:1 | 50:50 | 30.5 g | 83 |
| 15 | DMTMC | TMC:d,l-LA 1:1 | 80:20 | 29.8 g | 82 |
| 16 | DMTMC | TMC:DMTMC 1:1 | 60:40 | 17.3 g | 46 |
| 17 | DMTMC | TMC:DMTMC 1:1 | 60:40 | 29.9 g | 80 |
| 18 | DMTMC | TMC | 60:40 | 30.0 g | 84 |
| 19 | DMTMC | TMC | 80:20 | 27.7 g | 74 |
| 20 | DMTMC | TMC | 70:30 | 30.3 g | 83 |

| Sample Number | GPC Main Wt Av MW | Peak Disp. | GPC Overall Wt Av MW | Disp. | Tg | Tm | TMC by NMR % | (Theory) |
|---|---|---|---|---|---|---|---|---|
| 10 | 48,400 | 6.20 | 48,500 | 3.20 | | | | (38) |
| 11 | 112,000 | 8.06 | 92,000 | 2.30 | | | | (33) |
| 12 | 124,000 | 4.34 | 159,000 | 5.48 | | | | (18) |
| 13 | 196,000 | 4.90 | 194,000 | 20.80 | | | | (30) |
| 14 | 64,500 | 3.60 | 65,100 | 22.00 | | | | (25) |
| 15 | 102,000 | 2.40 | 101,700 | 4.28 | | | | (10) |
| 16 | 64,000 | 4.70 | 83,100 | 22.40 | −2° C. | 71° C. | 31.6 | (20) |
| 17 | 87,000 | 4.80 | 99,000 | 23.00 | 3° C. | 60° C. | 22.0 | (20) |
| 18 | 53,100 | 3.36 | 61,800 | 10.50 | −12° C. | | 44.0 | (40) |
| 19 | 113,000 | 3.60 | 105,000 | 22.60 | 0° C. | 71° C. | 23.6 | (20) |
| 20 | 51,500 | 4.10 | 84,800 | 24.30 | −3° C. | 59° C. | 31 | (30) |

*Sample 12 is a BAB block copolymer

TABLE VI
Tensile properties of Monofilament Fiber (tested at 23° C., 50% RH at 100% extension rate with 5 inch gauge length yarn samples average of ten or more measurements).

| Sample | Denier | Tensile Modulus grams/denier | Tensile Strength grams/denier | Ultimate Elongation % |
|---|---|---|---|---|
| 2A | 100 | 26 | 1.3 | 244 |
| 2B | 12 | 83 | 4.9 | 19 |
| 2C | 14 | 90 | 4.8 | 24 |
| 2D | 18 | 98 | 3.6 | 34 |
| 2E | 15 | 77 | 3.9 | 25 |
| 2F | 12 | 89 | 4.6 | 16 |
| 2G | 16 | 76 | 4.1 | 38 |
| 3A | 74 | 26 | 3.6 | 66 |
| 3B | 60 | 31 | 4.2 | 61 |
| 5A | 49 | 33 | 4.6 | 30 |
| 5B | 59 | 13 | 3.9 | 66 |
| 5C | 53 | 22 | 4.6 | 54 |
| 5D | 55 | 10 | 4.0 | 49 |
| 5E | 46 | 19 | 4.4 | 54 |
| 5E-1 | 52 | 9 | 4.3 | 57 |

TABLE VI-continued

Tensile properties of Monofilament Fiber
(tested at 23° C., 50% RH at 100% extension rate with 5 inch
gauge length yarn samples average of ten or more measurements).

| Sample | Denier | Tensile Modulus grams/denier | Tensile Strength grams/denier | Ultimate Elongation % |
|---|---|---|---|---|
| 5E-2 | 48 | 15 | 4.4 | 49 |
| 5E-3 | 42 | 30 | 5.2 | 34 |
| 5E-4 | 41 | 26 | 5.2 | 31 |
| 5E-5 | 47 | 32 | 5.2 | 23 |

EXAMPLE 28

ABA Block Copolymer of Trimethylene Carbonate (TMC), d,1-lactic Acid (d,1-LA) and 1-lactic Acid (1-LA)

An oven-dried, silanized glass 100 mL resin flask was equipped with mechanical stirrer and a glass paddle, argon inlet, a serum cap on one port, and a glass stopper on the remaining port. To the flask were added freshly dried and purified TMC (19.80 g, 194 mmol), d,1-Lactide (2.20 g, 15.3 mmol), and 2,2-dimethyl-1-3-propanediol (27 mg, 0.26 mmol). The flask was evacuated and filled with argon several times, then immersed in an oil bath at 150° C. Stirring was initiated, and after 5 minutes, 40 μL of a 1.0M solution of stannous octoate in toluene was added.

After one hour, a sample of the viscous polymer was removed and 1-Lactide (9.43 g, 65.4 mmol) was added through one port. Stirring was stopped after one hr., then heating stopped after an additional hr. The polymer was removed from the flask, dissolved in tetrahydrofuran (250 mL), precipitated into methanol (750 mL), and dried under vacuum at 50° C. Yield: 23.2 g (74%). Weight average molecular weight (relative to polysytrene standards) of the prepolymer=57,000; of the final polymer=107,000. Proton NMR analysis of the final polymer shows a TMC content of 50 mole percent (theoretical=55%). From the methine region of the proton NMR, one can estimate that about 74% of the lactic acid units are connected to other lactic acid units, compared to a theoretical value of 89.5% for a totally random B block and a totally homopolymer A block.

Similarly, two experiments were performed using this method to prepare other such block copolymers:

| ABA BLOCK COPOLYMERS OF TRIMETHYLENE CARBONATE (TMC), d, l-lactic acid (d,l-LA) and l-lactic acid (l-LA) | | | | | | |
|---|---|---|---|---|---|---|
| Sample No. | A Block | B Block | A:B Ratio | Quantity Isolated | Yield (%) | |
| 1 | l-LA | TMC:d,l-LA 9:1 | 30:70 | 21.2 g | 78 | |
| 2 | l-LA | TMC:d,l-LA 7.3:1 | 36:64 | 22.0 g | 72 | |

| Sample No. | GPC Main Peak Wt Av MW | Disp. | GPC Overall Wt Av Mw | Disp | Tg | Tm | % TMC by NMR (Theory) |
|---|---|---|---|---|---|---|---|
| 1 | 94,000 | 2.64 | 120,900 | 24.8 | −5° C. | 150° C. | 63 (63) |
| 2 | 86,800 | 1.72 | 80,800 | 1.72 | −10° C. | 156° C. | 56 (55) |

EXAMPLE 29

Completely Bioresorbable Graft-Fabrication:

1. Random copolymer compositions: Fiber "A"=97.5% DMTMC/2.5% TMC and Fiber "B"=98.2% DMTMC/1.8% caprolactone.

2. Fibers "A" and "B": as obtained from Examples 17 and 18.

3. Weaving: The 200 denier fiber was twisted 7.125 turn/inch when repackaged, to be used for the filling (horizontal) and wrap (vertical) construction to keep the monofilaments together. The fabrics were a plain weave tube with both warp and fill directions having the same fiber, at a construction of 120 total body ends by 120 picks per inch (that is a perfect square, tight weave). The total circumferences were 18.8 and 25.2 mm for each of the fibers used, which correspond to 6 and 8 mm diameter respectively. Some obviously defective areas were found from time to time due to slight changes of tension on the fill bobbin, and also due to the knots in the towed fiber.

4. The flat fabric was heat-set between 60° to 90° C. to round (cross section) with a glass mandrel and cleaned with 0.05% Triton X-100 detergent in 50% ethanol-water, then rinsed 6 times with water, and finally rinsed with absolute ethanol. The operation was performed inside a class 100 laminar flow hood up-to and including packaging of the device in sterilization pouches.

5. Room temperature ethylene oxide was used to sterilize these completely bioresorbable vascular grafts.

6. The water permeation rates at 120 mm Hg pressure after heat-set of such prostheses were below 500 cc/cm$^2$/minute. They were implanted bilaterally in sheep as carotid replacements without preclotting. No complications resulted.

Likewise, yarns made from the block copolymers such as those described and used in Example 40 can also be similarly fabricated into bioresorbable grafts.

EXAMPLE 30

Completely Bioresorbable Crimped and Coated Graft

1. Totally bioresorbable 6 mm vascular grafts were woven from Fiber "A"& "B" as described in Example 29, sections 1 to 3. Crimping according to the general method of Jekel (U.S. Pat. No. 3,337,673) was used. Thus, the spacer was provided by a cotton string helically wound on the fabric graft body with a glass mandrel inserted into the lumen. Crimp-shape was formed by slowly forcing the two ends of the graft towards the middle. The crimping can be set to as small as 0.5 millimeter up and 0.1 to 0.2 mm down so that the internal surface appears to be almost smooth but still resist kinking. After heat-setting, cleaning was done according to section 4 of Example 29.

A solution containing 2 to 3% coating polymer, e.g., the random copolymer of 91% TMC - 9% 1-lactide, was made with solvent dimethyl sulfoxide (DMSO). The clean bioresorbable graft was dipped into said solution six dips, inverting between each dip, to yield a 10% weight gain. In another example, when a 4.5% coating solution was used, 25% weight gain was obtained after nine dips. The dipping was performed inside a Class 100 laminar flow hood.

2. Standard room temperature cycle ethylene oxide was used to sterilize these completely bioresorbable coated and crimped vascular grafts.

3. The water permeation rates at 120 mm Hg pressure of such prostheses were about 400 cc/cm$^2$-minute. They were implanted bilaterally in sheep as carotid replacements without preclotting. No complications resulted. The patency rate at 12-week stands at 100% (6 out of 6 grafts) for these 6 mm, totally bioresorbable, crimped and coated vascular grafts.

EXAMPLE 31

Four 8 centimeter long pieces of human-implantable grade, crimped USCI Sauvage Bionit, vascular grafts manufactured by C. R. Bard, having a six millimeter diameter, were ultrasonicated with 0.05% Triton X-100 in 1:1 alcohol/water for sixty minutes at room temperature. The vascular protheses were then rinsed several times with deionized water, followed by two rinses with 95% ethanol and drying in a laminar blow hood equipped with high efficiency air filters. The dried vascular grafts were immersed into a solution of 1.40 grams of double-precipitated poly TMC (approx. 91,200 Daltons weight average molecular weight) in 140 mL of tetrahydrofuran, THF. The vascular grafts were inverted after each dip, allowed to dry, and weighed until the desirable weight gains were attained. A total of seven dips were performed for a 25% weight-gain. The dipping and packaging were performed inside the laminar flow hood. The protheses were subjected to room temperature ethylene oxide sterilization. The water permeation rate decreased from 1,500 to below 200 cc/cm$^2$ min. after the coating.

Under anethesia, light anticoagulation (during implantation) and sterile operating room conditions, two vascular grafts were implanted by end-to-end anastomoses without preclotting into both the left and right external carotid arteries of each of the two mixed adult domestic female sheep weighing approx. 50 kilograms. After twelve weeks of indwelling, all grafts were opened to blood flow when each animal was anticoagulated and sacrificed by euthanasia. The grafts were excised. All four recovered grafts with bioresorbable coatings were patent and displayed a thin, smooth pseudoneointimal layer on its luminal blood contacting surface.

Control Experiment. For comparison, the same procedure was performed with the Sauvage Bionit graft as received without coating. However, the grafts were preclotted just prior to insertion, a standard procedure used to diminish bleeding as suggested by the manufacturer. The patency rate was 15 out of 18 (83.33%). All luminar surfaces of the implants were covered with a much thicker layer of internal capsule and red thrombus as compared to the coated grafts described above.

EXAMPLE 32

Under the same operative and coating procedures described Example 31, a total of eight 8 centimeter long, six millimeter diameter Sauvage Bionit vascular grafts were coated with 25% weight-gain of a random copolymer of 91% TMC and 9% L-lactide (approx. 87,000 Dalton weight average MW) were implanted as bilateral carotid replacement in four adult female sheep.

After seven weeks, one of the four sheep was electively terminated and both grafts were patent and displayed pearl-like neointimal surfaces. The remaining three animals were kept to twelve weeks and electively terminated so as to be able to be compared to the control described in Example 31. All six excised grafts were patent and the blood contacting surfaces displayed smooth translucent pseudoneointimal layers.

EXAMPLE 33

Similar to Example 32, four similar eight centimeter long six millimeter diameter Sauvage Bionit vascular graft with the same coating polymer but 50% weight gain were implanted in two adult sheep as bilateral carotid replacements. One was electively terminated at seven weeks and the other at twelve weeks. All four excised grafts were patent at termination with pearl-like blood contacting surfaces.

EXAMPLE 34

Fibers extruded from Example 17 (that is random copolymer of 97.5% DMTMC and 2.5% TMC by weight) were towed to 180 denier and woven into six millimeter tubular fabric with 120 body ends per inch by 120 picks per inch. The fabric was crimped by first wrapping a cotton thread spirally around the tubular fabric supported with a pyrex glass rod as a mendrel, then compressed and heat-set at approx. 80° C. The experimental grafts were cleaned as previously described. The grafts were further coated with the random copolymer of 91% TMC and 9% L-lactide from a 2 wt % solution in dimethylsulfoxide which dissolved the coating copolymer but not the fabric fiber. The water permeation rates dropped from 300 cc/cm$^2$ min. to about zero after coating. A total of fourteen eight centimeter long six millimeter diameter completely bioresorbable vascular grafts, crimped and coated with 10% wt-gain, were implanted as bilateral carotid replacements in adult sheep as described in Example 31. One sheep died acutely (never recovered from anesthesia) for reasons unrelated to the grafts, as both grafts and the suture-lines were all intact. Five animals were kept to twelve weeks post operation and electively terminated. All ten excised vascular grafts were patent. The last animal was electively terminated after 24 weeks and both of the excised grafts were patent.

EXAMPLE 35

As in Example 34, six mm diameter vascular grafts were woven from yarns extruded from random copolymer with 95.6% DMTMC and 4.4% caprolactone. It was crimped, cleaned, coated and sterilized as described. A pair of such grafts, with 10% coating (copolymer of 91% TMC and 9% L-lactide) were implanted under sterile conditions, as described, into an adult sheep as bilateral carotid replacements. After eight weeks indwelling, the animal was electively terminated and the excised grafts were patent and the neointimal surfaces were thin and pearl-like.

EXAMPLE 36

Six Weavenit Dacron (Meadox Medical), crimped human implantable vascular grafts (4 mm diameter, 4 cm in length) were coated to 10% weight-gain with random copolymer of 91% TMC and 9% L-lactide in tetrahydrofuran solution. Water permeation rate dropped from 1,500 cc/cm$^2$ min. to 175 cc/cm$^2$ min when coating was equal to 10% of the initial weight.

The leak rate was considered to be tolerable without preclotting. After sterilization, they were implanted as carotid replacements in three mongrel dogs weighing approximately 22 kilograms each. Each dog received dipyridamole (25 mg) and aspirin (325 mg) beginning at 4 days preoperatively and continued for 2 weeks postoperatively so as to minimize the effect of sugery. All three animals were electively terminated at 4 weeks postoperatively (i.e., the subjects were with antiplatelet treatment for two weeks followed by two without such treatment). Four of the six grafts were found to be patent.

EXAMPLE 37

Similar to Example 36, four such Weavenit four millimeter diameter grafts were coated with the copolymer of 91% TMC and 9% L-lactide to 25% weight-gain. The water leakage rate dropped from 1500 cc/cm$^2$ min to almost zero. The grafts were implanted into two mongrel dogs given the same antiplatelet treatment for the pre- and post-operative periods. At four weeks post-operation, both animals were electively terminated and the four excised grafts were found to be patent.

EXAMPLE 38

Similar to Example 37, two Weavenit four millimeter diameter vascular grafts were coated with a homopolymer, poly TMC, to 25% wt-gain. The water permeation rate dropped from 150 cc/cc$^2$ min to almost zero. The grafts were implanted into a mongrel dog as bilateral carotid replacements. After four weeks post-operation, the animal was electively terminated and both grafts were found to be patent.

EXAMPLE 39

Fabrication of Rod and Ribbon as External Support For Dacron or Bioresorbable Vascular Grafts 1. An ABA block copolymer [A:B 70.30, A=polyDMTMC, B=1:1 random copolymer of DMTMC:TMC] was extruded at 220° C. in the modified Instron extruder with first a 1 mm diameter die onto a clean chrome plate. The unstretched round rod-shaped extrudate was coiled on the plate. The product was placed inside a laminar flow hood to allow for the copolymer to crystallize. After two days, the appearance of the rods changed from completely transparent to slightly hazy. The ca. 1 mm rod was stretched six-fold and then was attached to a 8 cm long piece of straight Weavenit knitted Dacron 4 mm vascular graft (Meadox Medical Inc. Catalog No. 07U004, Lot No. 237012) in a spiral fashion and fastened every 20° with 7-0 Prolene suture. The protheses was cleaned with 0.5% Triton X 100 in 50/50 water/ethanol in an ultrasonic bath for 1 hr. rinsed 6 times with deionized water, 2 times with 95% ethanol before it was hung in a laminar flow hood to air dry. A clean and dry 4 mm OD pyrex glass rod was inserted into the graft so that a good contact would be established between the knitted fabric and the external spiral support to enhance adhesion when the coating solution is applied. The coating solution contained 2% by weight of a random copolymer of 91% trimethylene carbonate and 9% L-lactide (wt average molecular weight=87K) in dimethyl sulfoxide. A total of eight dips were applied before the total weight gain reached 10%. The Prolene suture was later removed. The graft did not kink or collapse upon bending.

2. The block copolymer was similarly extruded but a die with a retangular orifice measuring 4.0 mm × 1.0 mm was used. When the extruded rod turned slightly milky white, ca. 6 inch. pieces were each stretched six and a half times of their original length and stabilized on a solid surface to allow the stretched plastic to set. The final size was 2.0 mm×0.5 mm. It was similarly attached to a 4 mm straight Weavenit Dacron vascular graft. The graft was also coated as before. The benefit of not kinking and collapsing was also achieved.

3. The same block copolymer was extruded in a similar fashion but the die size was changed to 4.0 mm × 0.50 mm. After aging and stretching, the final ribbon size was 2.0 mm×0.25 mm. It was attached to 4 mm diameter straight Weavenit Dacron vascular graft in the same manner and coated as before. The prosthesis stayed open when bent, and kinking or collapsing was avoided.

4. Similarly, the rod or ribbon can be applied to a completely bioresorbable graft since the bioresorbable yarn used to fabricate the totally bioresorbable graft was not affected by the dimethyl sulfoxide solvent.

EXAMPLE 40

Suture Fabrication

1. Using a 0.030" round hole die, ABA block copolymer [A:B=70:30=DMTMC: (1:1=DMTMC:TMC)] and the modified Instron as an extruder, fibers were extruded at 220° C. and with overall draw of 5.0, 5.5 and 5.8. The fibers were stored for 72 hrs., then further drawn five to one (which was close to the maximum) and held at that length for 72 hrs. The size of the final fiber met the U.S.P. specification for 6-0 synthetic suture.

2. Using a 0.060" round die and an ABA block copolymer [A:B=70:30=DMTMC: (1:1 DMTMC:TMC)] and the modified Instron as an extruder, fibers were extruded at 220° C. with overall draw at 40, 6.22 and 6.66. The fibers were stored for 48 hrs in the laminar flow hood. The fibers which had a 6.66 draw were further drawn five to one (which was the maximum) and held to that length for 72 hrs. The size of the final fiber met the U.S.P. specification for 5-0 synthetic suture.

3. Sutures and fibers from previous examples can also be coated, multiplyed or braided to be used in areas where higher mechanical strength, softer texture or better knot holding capability is desired.

EXAMPLE 41

Nerve Channel Extrusion

The fabrication of polycarbonates to nerve channels, tubes, or hollow fibers based on DMTMC with TMC or caprolactone or l-lactide with TMC type of copolymers in an ABA or BAB triblock structure where A is a DMTMC or l-lactide hard block and B, the rubbery block, is a copolymer of DMTMC with TMC or DMTMC with caprolactone, or TMC with or without lactides, was evaluated using the Instron Rheometer as a ram extruder and a tube in orifice type die. The hollow fiber or tube dimensions were controlled by the die dimensions, differential gas pressure between the inner and outer surfaces of the tube, melt draw down and subsequent orientation processes. Range of diameters was about 0.5 to about 3 mm internal diameter, with significant wall thickness to provide rigidity and strength for implantation into an animal or human.

Dies having the outer diameters of the center tube of about 1.5 mm and orifices ranging from 2.5–3.5 mm were used without an appreciable applied pressure differential. There was significant die swell during extrusion which provided inner tube diameters greater than 3 mm. Other desirable diameters were easily achieved by drawing.

EXAMPLE 42

Sample 10 from Table V, an A-B-A block copolymer of DMTMC (A block) and a 50/50 random copolymer of DMTMC and TMC (B block) was extruded into hollow fibers or tubes ranging from 0.5 to 2 mm in diameter using a tube-in-orifice die. The tubes were still somewhat tacky when dry, although they could be easily handled when wet. Tubes having 0.2 mm wall thickness for 1 mm OD would spring open when pressed together.

EXAMPLE 43

Sample 12 from Table V was B-A-B block copolymer of DMTMC (A block) and a 50/50 copolymer of DMTMC and TMC (B block). Because of its high molecular weight and related high melt viscosity, the polymer melt fractured when extruded. Satisfactory tubes could, however, be extruded at 220° C. The melt strength of this BAB structure was significantly lower than the A-B-A structure in Sample 11. The material also is more tacky than the ABA structure. However, tubes pinched close would reopen, indicating that a high molecular weight of the A block is desirable. Tube inner diameters of 0.5 to 3 mm were achieved.

EXAMPLE 44

An A-B-A block copolymer was made, Sample 13, Table V, where the A-block was DMTMC, and the B-block was a 50/50 random copolymer of DMTMC and TMC, with the B block molecular weight being the highest in this series of A-B-A polymers of DMTMC and TMC. This material extruded well at 180° C. and tube sizes ranging from inner diameters of 0.5 to 3 mm was achieved. Tack was lower than previous examples, and the dry tubes reopened when pinched closed.

EXAMPLE 45

Nerve Channel Fabrication via Solution Dipping

Samples ranging from 0.5 mm I.D.×0.75 mm O.D. to 3.0 mm I.D.×3.50 mm O.D. were routinely prepared by this method for use as nerve channels.

a. Mandrel materials included, e.g., Pyrex glass tubings, stainless steel (316) tubings or rods, platinum wires and tungsten wires or rods. They were selected partly because of their higher surface energy so that the polymer solution would spread evenly on their surfaces and partly because they were relatively inert so they can be cleaned easily and reused.

b. Solvents: Usually tetrahydrofuran and a few drops methyl ethyl ketone or methyl isobutyl ketone. Occasionally, chloroform or 1,4-dioxane was used as the primary solvent depending on the solubility of the polymer system.

c. Polymer solutions ranging from 1% to 15% by weight to solvent volume ratio have been used and the concentration was adjusted so that between 8 to 20 dips would give the desirable wall thickness. (The rule of thumb is that the larger the diameter, the thicker the wall will be needed to avoid collapsing. Therefore, either more dips would be required or a slightly more concentrate solution could be used.)

d. Time between dips was usually ten to thirty minutes. For a few polymer systems, the wall contracted after overnight drying. Thus, an additional one or two dips had to be performed the following morning, i.e., 15 to 16 hours later.

e. Molecular weight of polymer used (weight average) generally ranged from 10,000 to 250,000, as determined by GPC in tetrahydrofuran and calibrated with polystyrene standards. No significant or detectable change of molecular weight was recorded with the polycarbonates used, before and after fabrication.

f. Most of the protheses were cut to the desired lengths while still on the mandrel. Before demandreling, the protheses were soaked in methanol or methanol/water or water for an hour in the refrigerator. This helped to remove the protheses off the mandrel and demandreling was performed in a Class 100 laminar flow hood and handled with clean room grade gloves.

g. Sterilization was generally performed with ethylene oxide at room temperature.

In this manner, nerve channels from homopolymer, random or block copolymer were prepared.

EXAMPLE 46

Tendon and Ligament Replacement Devices

Tendon and ligament replacement devices can be fabricated from these biopolymer fibers by the following techniques.

A. Uniaxial towed fiber device

A bundle of well aligned fibers roughly with cross-sectional dimensions of 5–6mm by 0.4–0.5mm and with a length of 45 cm are fastened onto two surgical needles. The device is cleaned with 0.05% Trinton X-100 in 50% ethanol-water, then rinsed six times with water, and finally rinsed with absolute alcohol. The operation is performed inside a class 100 laminar flow hood from the cleaning of the device up to and including packaging of the device in sterilization bags. Room temperature ethylene oxide is used to sterilize these devices.

The device of this size is useful for tendon or ligament replacements in small animals, e.g., the Achilles tendon in rabbits.

B. Coated uniaxial towed fiber devices

A bundle of 44 yarns of Fiber F (a 220 denier yarn made from a 5 denier per filament fiber with tensile strength of 2.83g/d and spun from a 98% DMTMC-2% TMC random copolymer) was cleaned by ultrasonic bath with 0.05% Triton X-100 water-ethanol solution. It was rinsed thoroughly in deionized water, and then with absolute alcohol. After air drying in a laminar flow hood, the yarn was coated with a 7% DMSO solution of 91% TMC-9% l-lactide random copolymer of MW ~87,000. The yarn was coated by dipping into the solution. After air drying (over 7 hrs.), it was inverted and dip coated for a second time. Coating weight gain was determined to be 6%. For insertion of the two ends of the prosthesis through the eye of the surgical needle, the ends were coated four more times with the solution so that the individual filaments cannot be readily separated. After through air drying, the prosthesis was placed in a sterilization pack and sterilized with ethylene oxides. The prothesis made was ready for rabbit Achilles tendon replacement.

C. Coated unaxial towed fiber devices

Similarly, a coated device of the 91% TMC 9% l-lactide coating a high strength (extended chain) polyethylene fiber was constructed. A bundle of 14 Spectra 1000 medical grade extended chain polyethylene yarn (650 denier yarn) was cleaned and dried as above. A 0.3% tetrahydrofuran solution of the 91% TMC-9% l-lactide copolymer was used for dip coating. Dip coating twice allowed a weight gain of 3% which was sufficient to have most of the filaments adhere together but the prothesis was not coated too heavily to become rigid and kink. The two ends were also coated extra for ready needle insertion. After air drying and sterilization with ethylene oxide, the prothesis made was ready for replacing the rabbit Achilles tendon.

D. Braided and crocheted fabric devices

Six yarns of twisted fibers are braided together to form a strand of fabric 45mm in length and with cross-sectional dimensions of 1mm by 6mm. Similarly, yarns are crocheted into devices of various cross-sectional diameter and length, depending on the end application. These fabrics are cleaned as discussed above and are to be used as replacement devices for ligaments and tendons in small animals.

EXAMPLE 47

Wound Cover

Cloth type of materials made of the various bioresorbable fibres can be used. This includes woven and non-woven such as mesh, felt, cloth, knit, etc. After cleaning, adherence of these materials to a selective barrier is desirable. For example, a thin layer of medicalgrade silicone film can be used.

Alternatively, an asymmetric membrane with one tight surface from these biopolymers may be used with or without such a barrier film.

EXAMPLE 48

Nerve Channel Implantation Studies

Mouse Sciatic Nerve Regeneration

Adult anesthetized C57BL/6J mouse with a sciatic nerve transected had both the proximal stump and distal stump secured by a single 10-0 nylon suture and inserted into a 5-6mm length of a nerve channel tube made from polytrimethylene carbonate (MW~90,000) to give a final gap length of 3-4mm. Postoperatively, at 6 weeks, the sciatic nerve of the animal, appropriately perfused for tissue studies, was again exposed and retransected 3mm distal to the nerve guide tube. Nerve guides with enclosed regerated nerves were then dissected out, post-fixed in 2% osmium tetroxide and processed for plastic embedding (DER, Ted Pella Inc.). Just before embedding, the tissue was usually divided into several segments for sampling at multiple cross-section levels. For most implants, five levels were sampled by one micron sections. These levels were: proximal sciatic stump at 1 to 2 mm proximal to the implant; three levels (proximal, central, distal) within the tube through the original gap, and the distal stump 1 to 2 mm distal to the implant. Data obtained in the central section was used for comparison.

The results indicate that these channels do bioresorb and that they do not cause scar formation. They are as much or more vasotropic than the poly d,l-lactide channels. In addition, the epineurium of the regenerated nerve using these nerve guides is much thinner than that using the lactide guides and approximates the size of the intact nerve.

EXAMPLE 49

Assymmetric Membrance From Block Copolymer

An ABA block copolymer was used to prepare the asymmetric membrane; the B block was 1:1 dimethyltrimethylene carbonate (DMTMC):trimethylene carbonate (TMC), the A block was DMTMC homopolymer, and the A:B ratio was 70:30. The weight average (MW) was about 180,000. A sample of the polymer (5g) was dissolved in a mixture of tetrahydrofuran (35mL) and diglyme (5mL) and protected from drafts. The solvents were allowed to evaporate for about 4 hrs, then the plate was placed in an oven at 45°–50° C. overnight. The resulting film was removed from the plate and submitted for analysis by scanning electron microscopy. This showed that the film has a tight, smooth, non-porous side (the glass side), and a highly porous reverse side. Cross section of the film shows that there are many pores and channels thoroughout the bulk of the film except for the side of the tight skin. Films varying in thickness from about 80 to about 350 $\mu$m were prepared in this way.

EXAMPLE 50

Fabrication of Rod and Ribbon as Internal Support in Conjunction with Balloon Angioplasty An ABA block copolymer [A:B=80:20, A=DMTMC, B=1:9=DMTMC:TMC] was extruded at 190° C. in the modified Instron extruder, with either a round or a rectangular die. The rod or ribbon produced was stored in a Class 100 laminar flow hood for 48 hrs., before it was cold drawn to give an overall draw ratio of eight and six respectively. The product was wrapped around a 2mm diameter glass rod as mandrel, in a spiral fashion, and stabilized at both ends. Dimethyl sulfoxide was added dropwise to the "spiral" while the mandrel was rotating at 5 RPM by a motor in a horizontal position. After seven days, the product was removed from the mandrel. The spiral form of the product was retained. This type of completely bioresorbable "spring" can be used in conjunction with balloon angioplasty to help to maintain the patency of re-opened blood vessel, replacing clips or springs made of stainless steel or other materials.

EXAMPLE 51

Sample 2 from Example 28 was an ABA block copolymer with A:B ratio of 30:70 and with l-LA (A block) and a 9 and 1 copolymer of TMC and d,l-LA (B block). Elastic tubes, useful as nerve channels, fallopian tube replacements, were extruded at 200° C. similar to Example 41. Whenever the tubes were deliberately pinched close, they would reopen immediately. Tube inner diameters of 0.5 to 3mm were achieved.

EXAMPLE 52

Biopolymer Coated Polyurethane Devices

ComfaDerm KM-1422-00 (obtained from Semex Medical, Malvern, PA, USA), a medical grade foamed, flexible polyurethane coated on one side with a pressure sensitive medical adhesive, was coated from the other side with a 4% DMSO solution of 90% TMC/10% l-lactide random copolymer. Once the solution was applied evenly on the surface and subjected to 110° C. heating in an air oven, the solution soaked through the foam and, therefore coated the system, in a matter of minutes. Thorough drying for over 12 hrs afforded an evenly coated flexible foamed polyurethane based device.

Similarly, dimethylacetamide solution casted thin or thick films of polyurethane, e.g., Pellethane 2103-80AE and Pellethane X0119-70A (obtained from Upjohn Co.), were readily coated with a 4% DMSO biopolymer coating solution. Once the casted polyurethane film is casted, dried in an 120° C. oven, the DMSO coating solution was added onto the film while still hot. The solution had a tendency to adhere unevenly; however, with care in spreading the solution, and subjecting the system to heating in the oven, and repeating the spreading and heating cycle a few times over time, e.g., one hour, even coated surfaces were obtained. Strong adhesion was achieved as demonstrated by pin pricking and rubbing, which did not separate the two films.

EXAMPLE 53

Trimethylene Carbonate/l-Lactide [90/10] Random Copolymer.

In a 100 mL reaction flask fitted with mechanical stirrer and argon inlet were combined trimethylene carbonate (51.45g, 504mmol), l-lactide (8.07g, 56mmol), and 1,6-hexanediol (47mg, 0.40mmol). The flask was evacuated and filled with argon several times, immersed in an oil bath at 160° C. and stirring was initiated. After 10mins., the polymerization catalyst, 25 μL of 0.20M solution of tin(II) octoate in toluene, was added via syringe. The mixture was stirred at 160° C. for 4hrs., then the polymer was removed from the flask, dissolved in tetrahydrofuran (450mL), and precipitated into methanol (1200mL) in a blender. The precipitated polymer was stirred with additional methanol (400mL) in the blender, filtered, and dried in the vacuum oven at 50° C. Yield: 43.8g (74%). Weight average molecular weight=120,000 (polydispersity 1.5). Proton NMR (400MHz) shows a final composition of 80% trimethylene carbonate units and 20% lactic acid units (theoretical 82% and 18%, respectively). This polymer is especially useful as a coating polymer.

What is claimed is:

1. A medical device formed totally or in part of one or more biopolymers selected from the group consisting of block copolymers having at least one type of recurring monomeric unit of the following General Structures I and II:

Structure I

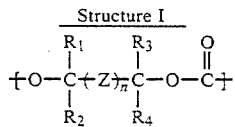

Structure II

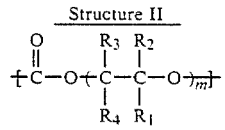

wherein:

Z is $-[C(R_5R_6)]-$, $-[NR_5]-$, $-O-$ or a combination thereof, where Z is selected such that there are no adjacent heteroatoms;

n is from 1 to about 8;

m is from 1 to about 8;

$R_1$, $R_2$, $R_3$, and $R_4$ are the same or different at each occurrence and are hydrogen, aryloxyalkyl, alkyoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylarly, alkoxyalkyl, or aryl or alkyl substituted with one or more substituents selected from the group consisting of alkyl, aryl, alkoxy, aryloxy, dialkylamino, diarylamino, and alkylarylamino; and $R_5$ and $R_6$ are the same or different and are $R_1$, $R_2$, $R_3$, $R_4$, dialkylamino, diarylamino, alkylarylamino, alkoxy, aryloxy, alkanoyl, or arylcarbonyl, or any two of $R_1$ to $R_6$ together may form an alkylene chain completing a 3, 4, 5, 6, 7, 8 or 9 membered alicyclic fused, spiro, bicyclic or tricyclic ring system or a combination thereof, which system may optionally include one or more non-adjacent carbonyl, oxa, alkylaza or arylaza groups;

with the proviso that when said biopolymers are copolymer having recurring units of the Structure I derived from trimethylene carbonate, the other recurring monomeric units of the copolymer are not derived from gylcolide or glycolic acid.

2. The device of claim 1 wherein $R_1$, $R_2$, $R_3$, $R_4$, $R_5$ and $R_6$ are the same or different and are selected from the group consisting of hydrogen, alkyl, cycloalkyl, alkylaryl, alkoxyalkyl, aryloxyalkyl, aryloxyaryl, aryl and arylalkyl groups, and aryl, arylalkyl or alkylaryl substituted with one or more alkyl, alkoxy and alkoxyalkyl groups.

3. The device of claim 2 wherein $R_1$, $R_2$, $R_3$, $R_4$, $R_5$ and $R_6$ are the same or different and are selected from the groups consisting of hydrogen, alkyl, cycloalkyl, alkylphenyl, alkoxyalkyl and phenylalkyl, and phenyl, alkylphenyl and phenylalkyl substituted with one or more alkyl or alkoxy groups.

4. The device of claim 3 wherein:

Z is $-[C(R_5R_6)]-$, $-O-$ or a combination thereof;

n is 1, 2, or 3;

m is 1, 2, 3, 4, 5 or 6; and $R_1$ to $R_6$ are selected from the group consisting of substitutents in which aliphatic moieties include up to about 10 carbon atoms and aryl moieties include up to about 16 carbon atoms.

5. The device of claim 1 wherein said biopolymers comprise at least one type of recurring monomeric units of the following general Structures II and III:

Structure II

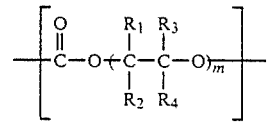

Structure III

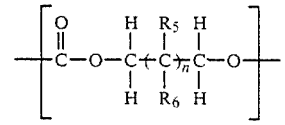

wherein:

n is 1 to about 3;

m is 1 to about 4;

$R_1$, $R_2$, $R_3$, $R_4$, $R_5$, and $R_6$ are the same or different and are hydrogen, aryl, alkylaryl, arylalkyl or alkyl, or $R_5$ and $R_6$ together may form an aliphatic chain having from about 3 to about 10 membered spiro, bicyclic, or tricyclic ring structure or a combination thereof.

6. The device of claim 5 wherein:
n is 1, 2 or 3;
m is 1, 2 or 3; and
$R_1$, $R_2$, $R_3$, $R_4$, $R_5$ and $R_6$ are the same or different and are hydrogen, alkyl, phenylalkyl or alkylphenyl.

7. The device of claim 6 wherein $R_1$, $R_2$, $R_3$, $R_4$, $R_5$ and $R_6$ are the same or different and are hydrogen or alkyl having from 1 to about 7 carbon atoms.

8. The device of claim 1 wherein the biopolymers comprises at least one type of recurring monomeric unit moieties selected from the group consisting of:

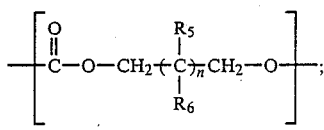

wherein:
$R_5$ and $R_6$ are the same or different and are hydrogen, alkyl, aryl, cycloalkyl, arylalkyl, alkoxyalkyl, aryloxyalkyl, or aryl or arylalkyl substituted with one or more alkyl or alkoxy groups alkoxy, alkanoyl, dialkylamino, or $R_5$ and $R_6$ together may form an alkylene chain completing a 4, 5, 6, 7, 8, 9 or 10 membered spiro, bicyclic, or tricyclic ring structure or a combination thereof, which structure may optionally include one or more non-adjacent divalent carbonyl, oxa, alkylaza or arylaza groups with the proviso that at least one of $R_5$ or $R_6$ is other than hydrogen; and n is 1, 2 or 3.

9. The device of claim 8 wherein $R_5$ and $R_6$ are the same or different and are phenyl, phenylalkyl, alkylphenyl, alkyl, or $R_5$ and $R_6$ together form alkylene a divalent chain forming a 4 to 8 membered ring structure.

10. The device of claim 9 wherein $R_5$ and $R_6$ together form a 5 to 7 membered spiro, or bicyclic ring structure or a combination thereof.

11. The device of claim 8 wherein $R_5$ and $R_6$ are the same.

12. The device of claim 11 wherein $R_5$ and $R_6$ are the same or different and are alkyl, phenyl, alkylphenyl or phenylalkyl.

13. The device of claim 8 wherein $R_5$ and $R_6$ are hydrogen.

14. The device of claim 12 wherein $R_5$ and $R_6$ are the same or different and are alkyl of from about 1 to 7 carbon atoms.

15. The device of claim 13 wherein $R_5$ and $R_6$ are alkyl of about 1 to 4 carbon atoms.

16. The device of claim 1 wherein the wt % of recurring monomeric units of the Structure I or Structure II included in said copolymer is at least about 50 wt % based on the total wt of monomeric units in the copolymer.

17. The device of claim 16 wherein said wt % is from about 80 wt % to about 100 wt %.

18. The device of claim 17 wherein said wt % is from about 85 to about 100 wt %.

19. The device of claim 18 wherein said wt % is from about 85 to about 99 wt %.

20. The device of claim 1 wherein said biopolymers are selected from the group consisting of copolymers comprising at least one type of recurring unit of the General Structures I and II, and at least other type of recurring monomeric units derived from the group consisting of substituted carbonates, non-substituted carbonates, lactones, dioxepanones, dioxanones other than carbonates, epoxides, epoxide/$CO_2$, anhydrides, orthoesters, and orthocarbonates.

21. The device of claim 1 wherein said copolymer comprises recurring monomeric units derived from 2,2-dimethyltrimethylene carbonate and other types of recurring monomeric units derived from orthocarbonates, orthoesters, lactones, trimethylene carbonates, ethylene carbonates and tetramethylene carbonates.

22. The device of claim 1 wherein said copolymer comprises recurring monomeric units derived from trimethylene carbonate and other types of recurring monomeric units derived from lactones.

23. The device of claim 1 which is a totally or partially bioresorbable medical device suitable for implantation in side of a living system to promote regeneration of body tissue.

24. The device of claim 1 which further comprises a biodurable portion.

25. A block copolymer comprising at least one type of recurring monomeric unit of the following General Structures I and II:

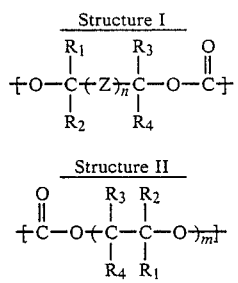

wherein:
Z is $-[C(R_5R_6)]-$, $-[NR_5]-$, $-O-$ or a combination thereof, where Z is selected such that there are no adjacent heteroatoms;
n is from 1 to about 8;
m is from 1 to about 8;
$R_1$, $R_2$, $R_3$, and $R_4$ are the same or different at each occurrence and are hydrogen, aryloxyalkyl, alkyoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylarly, alkoxyalkyl, or aryl or alkyl substituted with one or more biologically compatible substituents; and
$R_5$ and $R_6$ are the same or different and are $R_1$, $R_2$, $R_3$, $R_4$, dialkylamino, diarylamino, alkylarylamino, alkoxy, aryloxy, alkanoyl, or arylcarbonyl, or any two of $R_1$ to $R_6$ together may form an alkylene chain completing a 3, 4, 5, 6, 7, 8 or 9 membered alicyclic fused, spiro, bicyclic or tricyclic ring system or a combination thereof, which system may optionally include one or more non-adjacent carbonyl, oxa, alkylaza or arylaza groups;
with the proviso that when said copolymers have recurring units of the Structure I derived from trimethylene carbonate, the other recurring monomeric units of copolymer are not derived from gylcolide or glycolic acid.

26. The block copolymer of claim 25 wherein $R_1$, $R_2$, $R_3$, $R_4$, $R_5$, and $R_6$ are the same or different and are selected from the groups consisting of hydrogen, alkyl, cycloalkyl, alkylphenyl, alkoxyalkyl and phenylalkyl, and phenyl, alkylphenyl and phenylalkyl substituted with one or more alkyl or alkoxy groups.

27. The block polymer of claim 26 wherein:
Z is $-\{C(R_5R_6)\}-$, $-O-$ or a combination thereof;
n is 1, 2, or 3;
m is 1, 2, 3, 4, 5 or 6; and
$R_1$ to $R_6$ are selected from the group consisting of substituents in which aliphatic moieties include up to about 10 carbon atoms and aryl moieties include up to about 16 carbon atoms.

28. The block copolymer of claim 25 comprising at least one type of recurring monomeric unit of the following general Structures II and III:

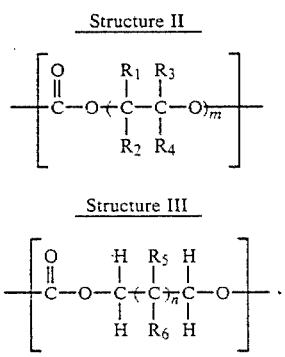

wherein:
n is 1 to about 3;
m is 1 to about 4;
$R_1$, $R_2$, $R_3$, $R_4$, $R_5$, and $R_6$ are the same or different and are hydrogen, aryl, alkylaryl, arylalkyl or alkyl, or $R_5$ and $R_6$ together may form an aliphatic chain having from about 3 to about 10 membered spiro, bicyclic or tricyclic ring structure or a combination thereof.

29. The block copolymer of claim 28 wherein:
n is 1, 2 or 3;
m is 1, 2 or 3; and
$R_1$, $R_2$, $R_3$, $R_4$, $R_5$ and $R_6$ are the same or different and are hydrogen, alkyl, phenylalkyl or alkylphenyl.

30. The block copolymer of claim 29 wherein $R_1$, $R_2$, $R_3$, $R_4$, $R_5$ and $R_6$ are the same or different and are hydrogen or alkyl having from 1 to about 7 carbon atoms.

31. The block copolymer of claim 30 comprising at least one type of recurring monomeric unit of the following Structure III:

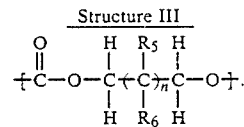

32. The block copolymer of claim 31 wherein $R_5$ and $R_6$ are the same or different and are hydrogen or alkyl having from 1 to about 4 carbon atoms.

33. The block copolymer of claim 25 wherein the wt % of recurring monomeric units of the Structure I or Structure II included in said copolymer is at least about 50 wt % based on the total weight of monomeric units in the copolymer.

34. The block copolymer of claim 33 wherein said wt % is from about 80 wt % to about 100 wt %.

35. The block copolymer of claim 34 wherein said wt % is from about 85 to about 99 wt %.

36. The block copolymer of claim 25 wherein said copolymer comprises at least one type of recurring unit of the General Structures I and II, and at least one other type of recurring monomeric unit derived from the group consisting of substituted carbonates, non-substituted carbonates, lactones, dioxepanones, dioxanones other than carbonates, epoxides, anhydrides, epoxide/-$CO_2$, orthoesters, and orthocarbonates.

37. The block copolymer of claim 36 wherein said copolymer comprises recurring monomeric units derived from 2, 2-dimethyltrimethylene carbonate and at least one other type of recurring monomeric unit derived from orthocarbonates, orthoesters, lactones, trimethylene carbonates, ethylene carbonates or tetramethylene carbonates.

38. The block copolymers of claim 37 wherein said copolymer comprises recurring monomeric units derived from trimethylene carbonate and recurring monomeric units derived from lactones.

* * * * *

UNITED STATES PATENT AND TRADEMARK OFFICE
CERTIFICATE OF CORRECTION

PATENT NO. : 4,920,203

DATED : April 24, 1990

Figure 2:
Figure 3:
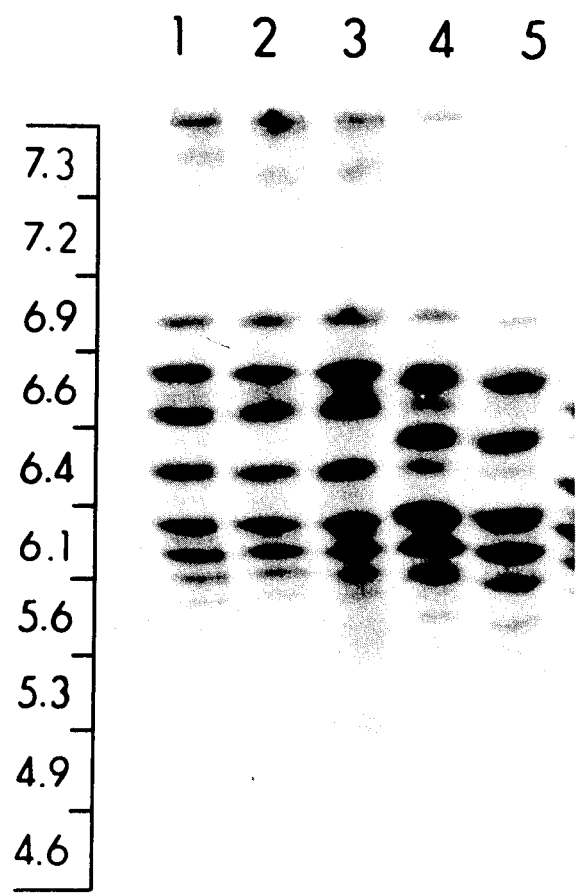
Figure 4:
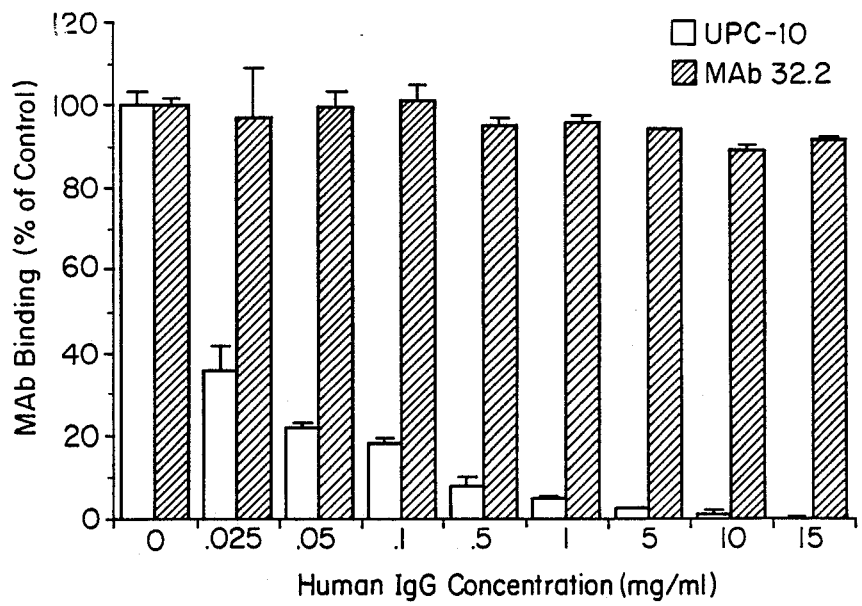
Figure 4B:
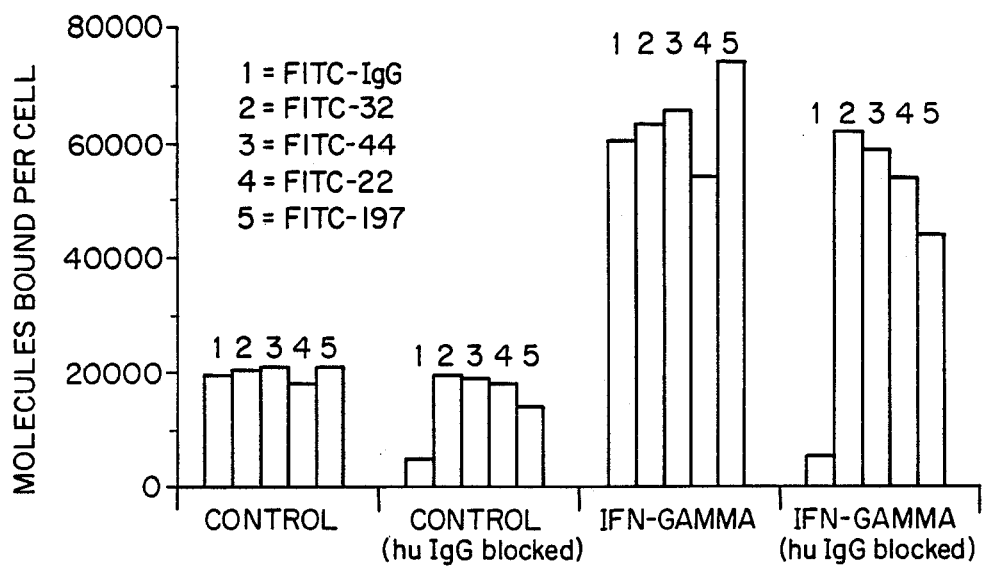
Figure 5A:
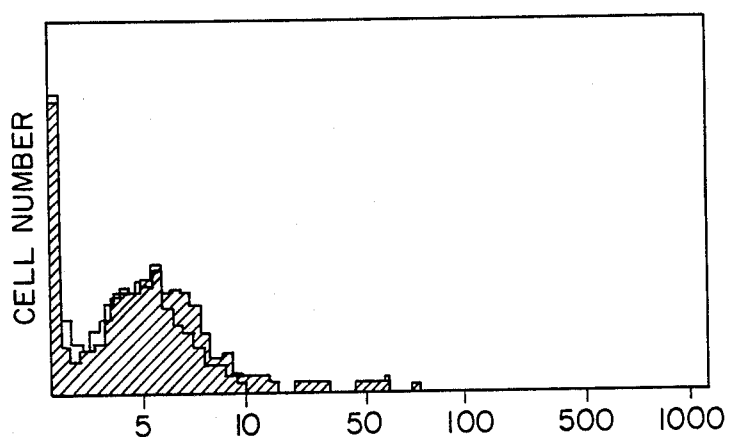
Figure 5B:
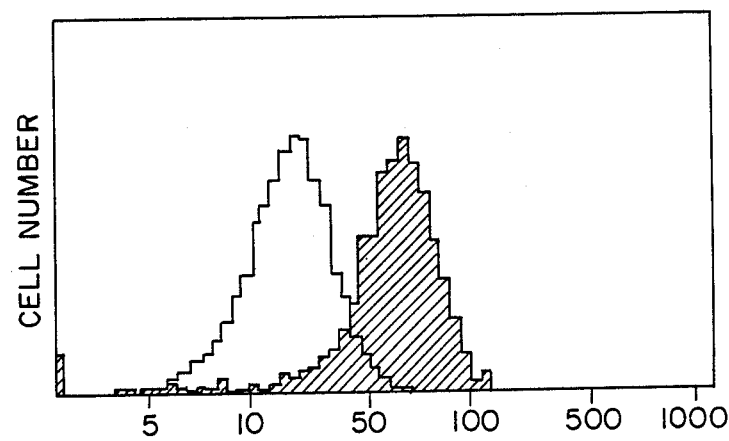
Figure 5C:
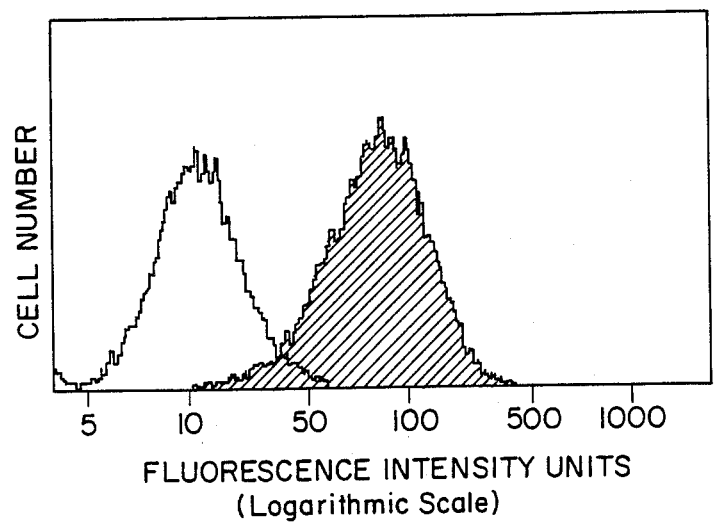
Figure 6:
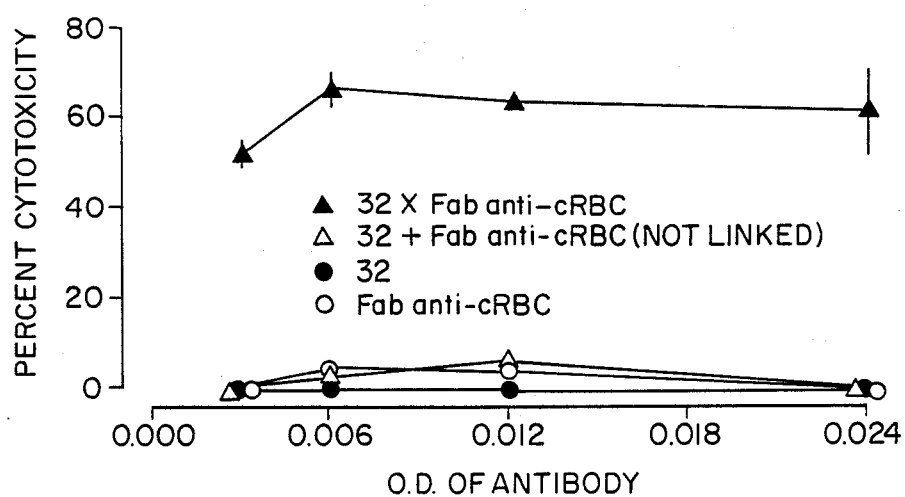
Figure 7:
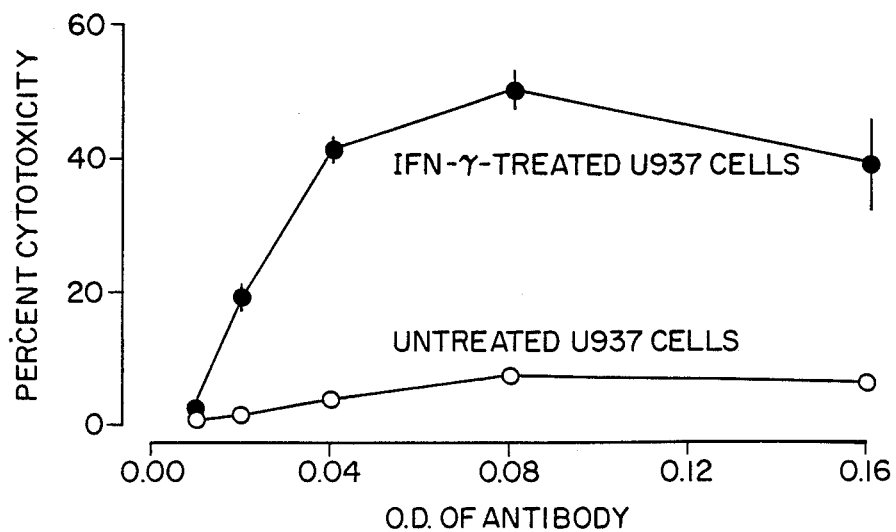
Figure 8:
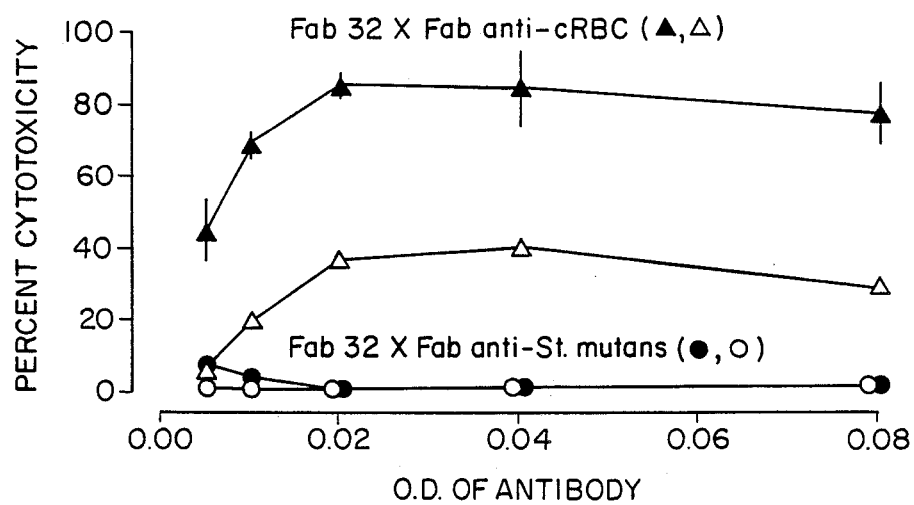
Figure 9:
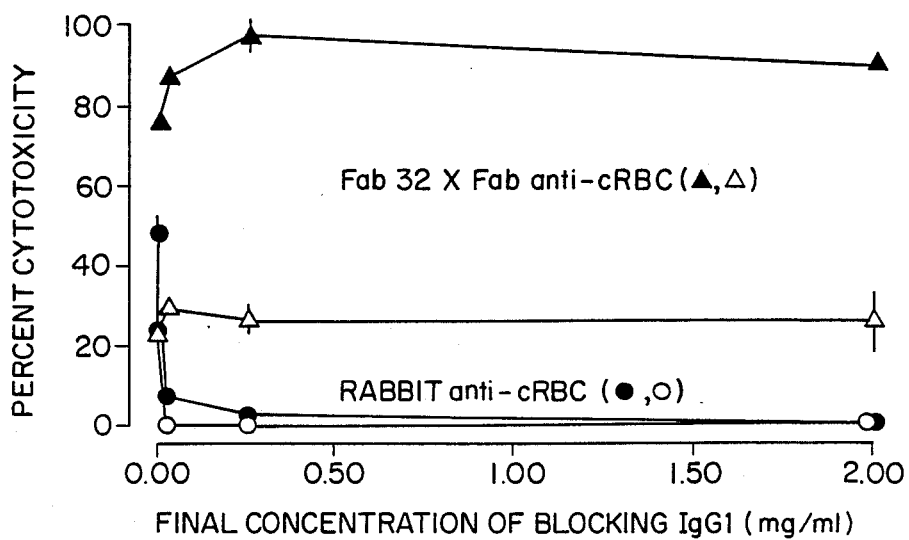
Figure 10:
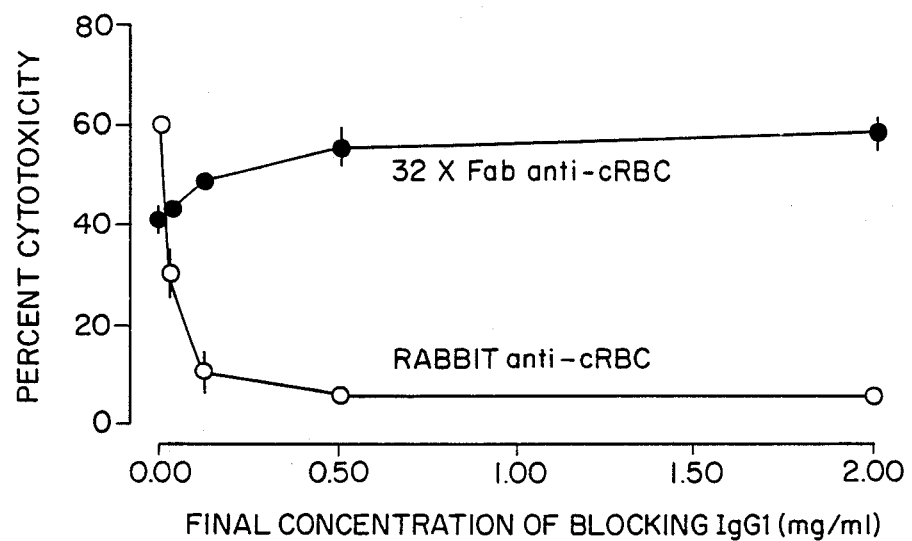

INVENTOR(S) : Reginald T. Tang, Frank Mares, William J. Boyle, Jr., Tin-Ho Chiu and Kundabhai M. Patel It is certified that error appears in the above-identified patent and that said Letters Patent is hereby corrected as shown below:

Figs. 1 to 10, sheets 1 of 8 to 8 of 8, should be deleted they are not part of this patent.

Signed and Sealed this

Tenth Day of September, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,920,203
DATED : April 24, 1990
INVENTOR(S) : Reginald T. Tang, Frank Mares, William J. Boyle, Tin-Ho Chiu and Kundan M. Patel It is certified that error appears in the above-identified patent and that said Letters Patent is hereby corrected as shown below:

IN THE CLAIMS

Col. 43, line 47, substitute ---or--- for "and" appearing after "General Structures I" and before "II:".

Col. 44, line 45, substitute ---or--- for "and" appearing after "General Structures I" and before "II:".

Col. 46, line 24, substitute ---or--- for "and" appearing after "General Structures I" and before "II:".

Col. 47, line 16, substitute ---or--- for "and" appearing after "General Structures I" and before "II:".

Signed and Sealed this

Twenty-first Day of February, 1995

Attest:

BRUCE LEHMAN

*Attesting Officer*      *Commissioner of Patents and Trademarks*